United States Patent
Agus et al.

(10) Patent No.: US 12,354,012 B2
(45) Date of Patent: Jul. 8, 2025

(54) HISTOPATHOLOGY CLASSIFICATION THROUGH MACHINE SELF-LEARNING OF "TISSUE FINGERPRINTS"

(71) Applicant: UNIVERSITY OF SOUTHERN CALIFORNIA, Los Angeles, CA (US)

(72) Inventors: David Agus, Los Angeles, CA (US); Daniel Ruderman, Los Angeles, CA (US); Rishi Rawat, Los Angeles, CA (US); Fei Sha, Los Angeles, CA (US); Darryl Shibata, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 582 days.

(21) Appl. No.: 17/437,158

(22) PCT Filed: Mar. 9, 2020

(86) PCT No.: PCT/US2020/021667
§ 371 (c)(1),
(2) Date: Sep. 8, 2021

(87) PCT Pub. No.: WO2020/185660
PCT Pub. Date: Sep. 17, 2020

(65) Prior Publication Data
US 2022/0180518 A1    Jun. 9, 2022

Related U.S. Application Data

(60) Provisional application No. 62/815,736, filed on Mar. 8, 2019.

(51) Int. Cl.
*G06T 7/00* (2017.01)
*G01N 33/574* (2006.01)
(Continued)

(52) U.S. Cl.
CPC ........... *G06N 3/088* (2013.01); *G01N 33/574* (2013.01); *G06T 7/0014* (2013.01);
(Continued)

(58) Field of Classification Search
CPC ......... G06T 7/0014; G06T 2207/20081; G06T 2207/20084; G06T 2207/30024;
(Continued)

(56) References Cited

U.S. PATENT DOCUMENTS 10,019,656 B2    7/2018  Huang et al.
2010/0088264 A1  4/2010  Teverovskiy et al.
(Continued)

FOREIGN PATENT DOCUMENTS

WO    2018/165103       9/2018
WO    2019/026081 A3    2/2019

OTHER PUBLICATIONS

Gertych, A. et al., "Convolutional neural networks can accurately distinguish four histologic growth patterns of ung adenocarcinoma in digital slides," Scientific Reports, 2019, 9:1483, 12 pgs.
(Continued)

*Primary Examiner* — Ming Y Hon
(74) *Attorney, Agent, or Firm* — Brooks Kushman P.C.

(57) ABSTRACT

Histologic classification of pathology specimens through machine learning is a nascent field which offers tremendous potential to improve cancer medicine. Its utility has been limited, in part because of differences in tissue preparation and the relative paucity of well-annotated images. We introduce tissue recognition, an unsupervised learning problem analogous to human face recognition, in which the goal is to identify individual tumors using a learned set of histologic features. This feature set is the "tissue fingerprint." Because only specimen identities are matched to fingerprints, constructing an algorithm for producing them is a self-learning
(Continued)

task that does not need image metadata annotations. Here, we provide an algorithm for self-learning tissue fingerprints, that, in conjunction with color normalization, can match hematoxylin and eosin stained tissues to one of 104 patients with 93% accuracy. We applied this identification network's internal representation as a tissue fingerprint for use in predicting the molecular status of an individual tumor (breast cancer clinical estrogen receptor (ER) status). We describe a fingerprint-based classifier that predicts ER status from whole-slides with high accuracy (AUROC=0.90), and is an improvement over traditional transfer learning approaches. The use of tissue fingerprinting for digital pathology as a concise but meaningful histopathologic image representation enables a new range of machine learning algorithms leading to increased information for clinical decision making in patient management.

23 Claims, 15 Drawing Sheets

(51) Int. Cl.
| | | |
|---|---|---|
| *G06N 3/088* | (2023.01) | |
| *G06V 10/764* | (2022.01) | |
| *G06V 10/82* | (2022.01) | |
| *G06V 20/69* | (2022.01) | |
| *G06V 40/14* | (2022.01) | |
| *G16H 50/20* | (2018.01) | |
| *G16H 50/70* | (2018.01) | |

(52) U.S. Cl.
CPC ............ *G06V 10/764* (2022.01); *G06V 10/82* (2022.01); *G06V 20/69* (2022.01); *G16H 50/20* (2018.01); *G16H 50/70* (2018.01); *G06T 2207/20081* (2013.01); *G06T 2207/20084* (2013.01); *G06T 2207/30024* (2013.01); *G06V 40/14* (2022.01)

(58) Field of Classification Search
CPC ........ G06T 2207/10056; G06T 7/0012; G06V 10/764; G06V 10/82; G06V 20/69; G16H 50/20; G16H 50/70; G16H 20/10; G06N 3/084
See application file for complete search history.

(56) References Cited

U.S. PATENT DOCUMENTS

| | | | |
|---|---|---|---|
| 2016/0019337 A1 | 1/2016 | Roberts et al. | |
| 2016/0292855 A1* | 10/2016 | Metzger | G06T 7/0012 |
| 2018/0082043 A1* | 3/2018 | Witchey | G06Q 10/0633 |
| 2019/0197368 A1* | 6/2019 | Madani | G16H 30/40 |
| 2019/0228312 A1* | 7/2019 | Andoni | G06F 18/2433 |
| 2019/0365265 A1* | 12/2019 | Grouchy | G06N 3/08 |
| 2019/0384047 A1* | 12/2019 | Johnson | G06V 10/764 |
| 2020/0163641 A1* | 5/2020 | Amit | A61B 6/502 |
| 2020/0211236 A1* | 7/2020 | Zhang | G06T 11/005 |
| 2020/0294278 A1* | 9/2020 | Watanabe | G06T 5/50 |
| 2023/0385643 A1* | 11/2023 | Rahman | G06N 3/082 |

OTHER PUBLICATIONS

Rivenson, Y. et al., "Deep learning-based virtual histology staining using auto-fluorescence of label-free tissue," 2018 (retrieved from https://arxiv.org/ftp/arxiv/papers/1803/1803.11293.pdf, 16 pgs.

Xu, Y. et al., "Large Scale issue Histopathology Image Classification, Segmentation, and Visualization via Deep Convolutional Activation Features," BMC Bioinformatics 18, Article No. 281, May 2017, 17 pgs.

International Search Report dated Jul. 1, 2020 for PCT Appn. No. PCT/US2020/021667, 4 pgs.

EP Search Report & Written Opinion dated Oct. 19, 22 for EP Appn. No. 20769831.7, 10 pgs.

* cited by examiner

Table 1. Fingerprinting Datasets

| Tissue Microarray Slides | Training | | | Testing | |
|---|---|---|---|---|---|
| | Slide 1 | Slide 2 | Slide 3 | Slide 4 | Slide 5 |
| Section name | BR20823_BM | BR20823_16 | BR20823_17 | BR20819_BM | BR20819_42 |
| TMA section number | 27 | 16 | 17 | 84 | 42 |
| n patients from 20823 | 104 | 104 | 104 | 0 | 0 |
| n patients from 20819 | 0 | 0 | 0 | 104 | 104 |
| n cores | 207 | 207 | 207 | 208 | 208 |
| Site performing H&E stain | US Biomax Inc. | USC | USC | US Biomax Inc. | USC |
| Original scan resolution | 0.5 μm/pixel | 0.24 μm/pixel | 0.24 μm/pixel | 0.5 μm/pixel | 0.24 μm/pixel |

*Fig. 3*

| ROI | ROC AUC score |
|---|---|
| all patches | 0.88 |
| epithelium only (green) | 0.88 |
| stroma only (blue) | 0.83 |
| fat only (yellow) | 0.80 |
| epithelium AND stroma | 0.89 |

HISTOPATHOLOGY CLASSIFICATION THROUGH MACHINE SELF-LEARNING OF "TISSUE FINGERPRINTS"

CROSS-REFERENCE TO RELATED APPLICATIONS

This application is the U.S. national phase of PCT Appln. No. PCT/2020/021667 filed Mar. 9, 2020, which claims the benefit of U.S. provisional application Ser. No. 62/815,736 filed Mar. 8, 2019, the disclosures of which are hereby incorporated in their entirety by reference herein.

TECHNICAL FIELD

In at least one aspect, the present invention is related to machining learning methods for histopathological and clinical outcome based on histopathological feature classification of tissue samples.

BACKGROUND

Although deep learning (DL) has the potential to teach us novel aspects of biology, the most impressive use cases to date recapitulate patterns that experts already recognize.[1-6] While these approaches may improve inter-observer variability and accelerate clinical workflows, our goal is to use DL to learn how morphology from hematoxylin and cosin (H&E) images can be used to predict biomarkers,[7] prognosis[8] and theragnosis—tasks which are not currently possible for a pathologist to do by eye, but if possible, could improve our understanding of cancer biology. However, since DL learns from data, it needs large training sets to learn patterns. One of the biggest challenges is obtaining large, well-annotated training sets.

While typical computer vision datasets contain on the order of millions of annotated images to learn statistically significant relationships,[1] clinical pathology case sets generally number in the hundreds. Moreover, noise in the clinical annotations dilutes the learning signal and increases the probability the network will learn spurious features like stain color, clinical site, or other technical variations.[9-11]

Accordingly, there is a need for improved methods for implementing machine-learned histopathologic classification.

SUMMARY

In at least one aspect, a machining learning technique in which pre-training allows neural networks to learn histology-optimized features is provided. The method includes a step of training an untrained machine learning device executing a neural network to form a trained machine learning device. The training is accomplished by receiving a digital image of a histologic sample as input to a tissue fingerprinting function and outputting a vector of numbers called a tissue fingerprint that describes histologic patterns within the digital image and training the untrained machine learning device with digital images from a plurality of characterized or uncharacterized stained tissues samples. Characteristically, the untrained machine learning device learning the tissue fingerprinting function through an optimization procedure that minimizes an objective loss function that includes a first component promoting learning of the tissue fingerprinting function that can be used to match digital image patches from the same sample but distinguish digital image patches from multiple samples and an optional second component of the objective loss function promoting learning of the tissue fingerprinting function that is invariant to sources of pathology artifacts that are encountered during tissue processing. The method also includes a step of predicting a status of a stained tissue sample of unknown status by obtaining a sample digital image for a stained tissue sample of unknown status, applying the trained machine learning device to the sample digital image to determine a predicted tissue fingerprint for the stained tissue sample of unknown status, and finding a best match of the predicted tissue fingerprint to a set of tissue fingerprints for samples of known status.

In still another aspect, clinical estrogen receptor (ER), progesterone receptor (PR), and Her2 status in breast cancer were evaluated with the methods set forth herein. These biomarkers are important predictive and prognostic molecular markers currently assessed by molecular Immunohistochemistry (IHC) staining.[14]

BRIEF DESCRIPTION OF THE DRAWINGS

FIG. 3. Table 1 providing Fingerprinting Datasets.

FIGS. 7B-1, 7B-2, and 7B-3. B: Receiver operating characteristic curves (ROC) for clinical ER (left), PR (center), and Her2 prediction (right). The TCGA ROC curve reflects a test set from five-fold cross-validation, and the AUC corresponds to the average area under the ROC curves of all five TCGA test sets. All samples in the ABCTB dataset are test samples and were never seen during training. Sample sizes vary depending on the availability of clinical annotations FIGS. 8A, 8B, and 8C. a: Histogram of ER-predictions from the TCGA test set averaged across the entire slide (AUC=0.88). B: AUC scores obtained by pooling ER predictions from different regions within slides. C: Representative heatmaps of correctly and incorrectly classified whole slides. WSI prediction was obtained by averaging over all patches (epithelium, stroma, fat). Each slide visualization consists of an RGB thumbnail, a tissue type segmentation, and an ER prediction heatmap.

DETAILED DESCRIPTION

Figure 1A:
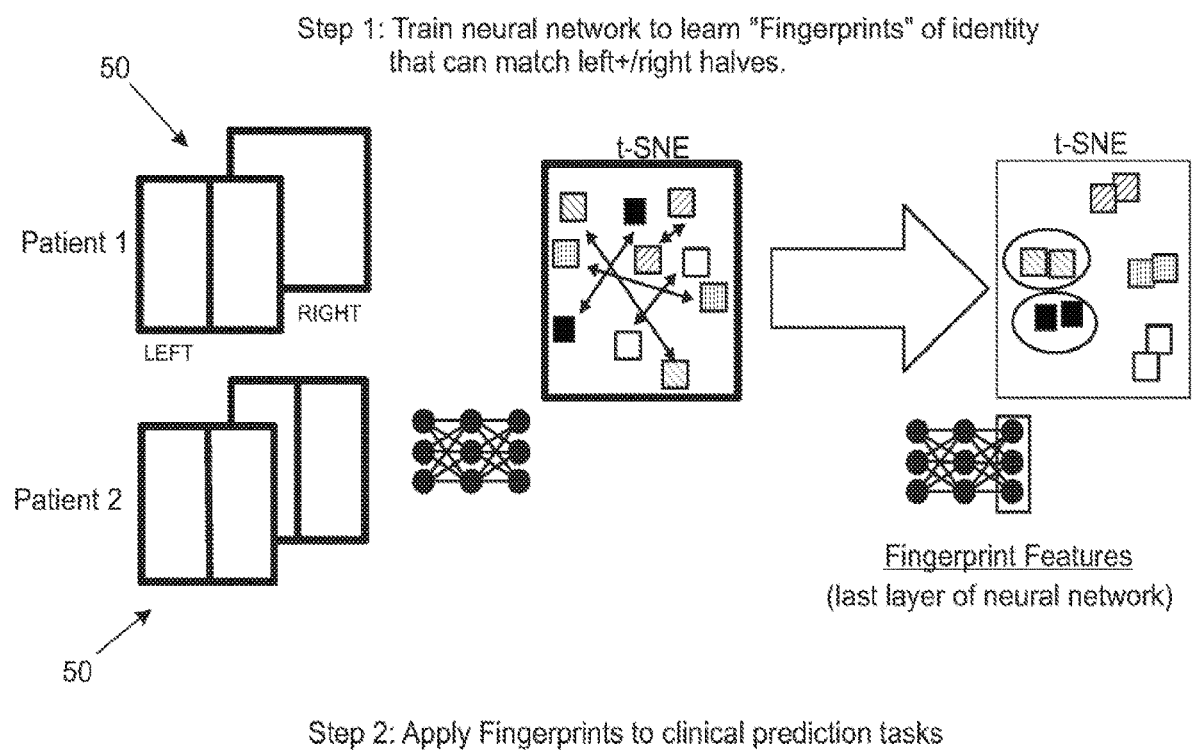
FIG. 1A. Networks are first trained to learn tissue fingerprints, which are patterns of cells and tissue visible on H&E images that can be used to distinguish between patients. Following this training internship, which can be scaled to very large numbers of patients without clinical outcome annotations, the fingerprints are repurposed to make clinically relevant predictions from small labeled datasets.

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

As used herein, the term "about" means that the amount or value in question may be the specific value designated or some other value in its neighborhood. Generally, the term "about" denoting a certain value is intended to denote a range within +/−5% of the value. As one example, the phrase "about 100" denotes a range of 100+/−5, i.e. the range from 95 to 105. Generally, when the term "about" is used, it can be expected that similar results or effects according to the invention can be obtained within a range of +/−5% of the indicated value.

The term "and/or" means that either all or only one of the elements of said group may be present.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

The phrase "composed of" means "including" or "consisting of." Typically, this phrase is used to denote that an object is formed from a material.

With respect to the terms "comprising," "consisting of," and "consisting essentially of," where one of these three terms is used herein, the presently disclosed and claimed subject matter can include the use of either of the other two terms.

The term "one or more" means "at least one" and the term "at least one" means "one or more." The terms "one or more" and "at least one" include "plurality" as a subset.

The term "substantially," "generally," or "about" may be used herein to describe disclosed or claimed embodiments. The term "substantially" may modify a value or relative characteristic disclosed or claimed in the present disclosure. In such instances, "substantially" may signify that the value or relative characteristic it modifies is within ±0%, 0.1%, 0.5%, 1%, 2%, 3%, 4%, 5% or 10% of the value or relative characteristic.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100. Similarly, when any range is called for, intervening numbers that are increments of the difference between the upper limit and the lower limit divided by 10 can be taken as alternative upper or lower limits. For example, if the range is 1.1, to 2.1 the following numbers 1.2, 1.3, 1.4, 1.5, 1.6, 1.7, 1.8, 1.9, and 2.0 can be selected as lower or upper limits. In the specific examples set forth herein, concentrations, temperature, and reaction conditions (e.g. pressure, pH, etc.) can be practiced with plus or minus 50 percent of the values indicated rounded to three significant figures. In a refinement, concentrations, temperature, and reaction conditions (e.g., pressure, pH, etc.) can be practiced with plus or minus 30 percent of the values indicated rounded to three significant figures of the value provided in the examples. In another refinement, concentrations, temperature, and reaction conditions (e.g., pH, etc.) can be practiced with plus or minus 10 percent of the values indicated rounded to three significant figures of the value provided in the examples.

The term "computing device" refers generally to any device that can perform at least one function, including communicating with another computing device. Sometimes the computing device is referred to as a computer.

When a computing device is described as performing an action or method step, it is understood that the computing devices are operable to perform the action or method step typically by executing one or more lines of source code. The actions or method steps can be encoded onto non-transitory memory (e.g., hard drives, optical drive, flash drives, and the like).

The term "neural network" refers to a machine learning model that can be trained with training input to approximate unknown functions. In a refinement, neural networks include a model of interconnected digital neurons that communicate and learn to approximate complex functions and generate outputs based on a plurality of inputs provided to the model.

The term "subject" or "patient" refers to a human or other animals, including birds and fish as well as all mammals such as primates (particularly higher primates), horses, birds, fish sheep, dogs, rodents, guinea pigs, pig, cat, rabbits, and cows.

The term "biomarker" refers to any biological property, biochemical feature, or aspect that can be used to determine the presence or absence and/or the severity of a disease or disorder such as cancer.

Throughout this application, where publications are referenced, the disclosures of these publications in their entireties are hereby incorporated by reference into this application to more fully describe the state of the art to which this invention pertains.

Abbreviations:
"ABCTB" means the Australian Breast Cancer Tissue Bank.
"AUC" means the area under the curve.
"ER" means estrogen receptor.
"H&E" means Hematoxylin and eosin.
"HER2" means human epidermal growth factor receptor-2.
"NN" means neural network.
"PR" means progesterone receptor.
"USC" means the University of Southern California.
"TCGA" means The Cancer Genome Atlas.
"TMA" means tissue microarray.
"IHC" means immunohistochemistry.

In general, the present invention provides a machining learning method in which pre-training on histology images allows neural networks to learn histology-optimized features that would improve performance on subsequent clinical classification tasks. In achieving this goal, the concept of "tissue fingerprints" is introduced. Tissue fingerprints are based on the hypothesis that molecular differences of the tumor are often translated into subtle differences in morphologic phenotypes. This idea is akin to the paradigm of precision medicine, where instead of grouping patients, individual patients are treated based on their specific molecular and environmental parameters. Hence, instead of training a network to distinguish between groups of samples, we first pre-configure the network to recognize, or "fingerprint," individual tumors, a task which can leverage large, unannotated datasets, which are widely available. After pretraining a network to fingerprint tissues, we expect that a smaller amount of annotated data will be necessary to adapt it to a clinical task.

Figure 7A:
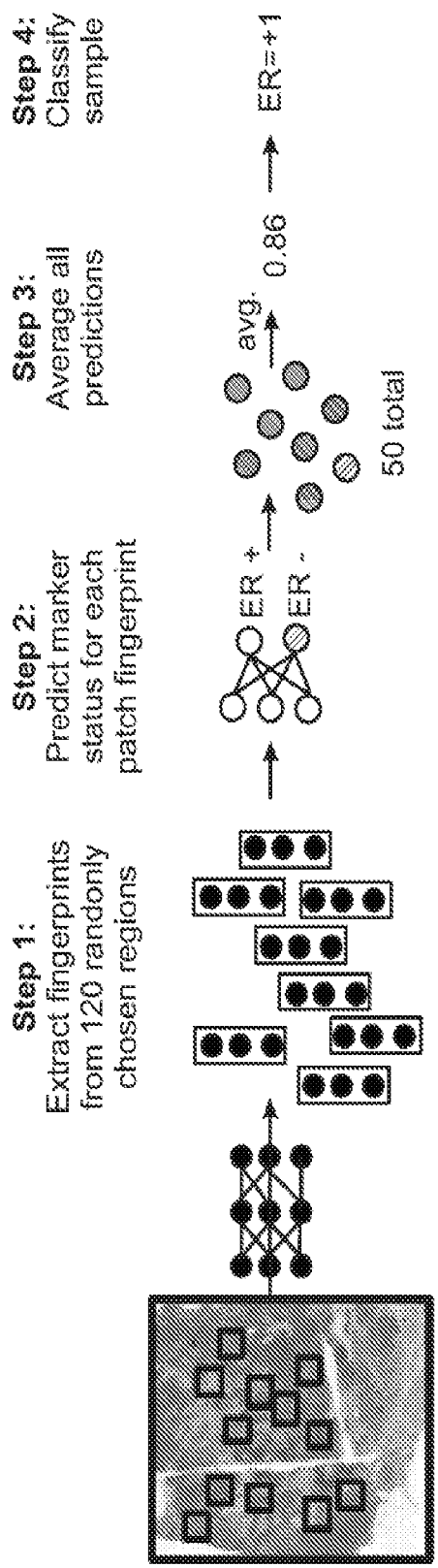
Figures 1, 7B:
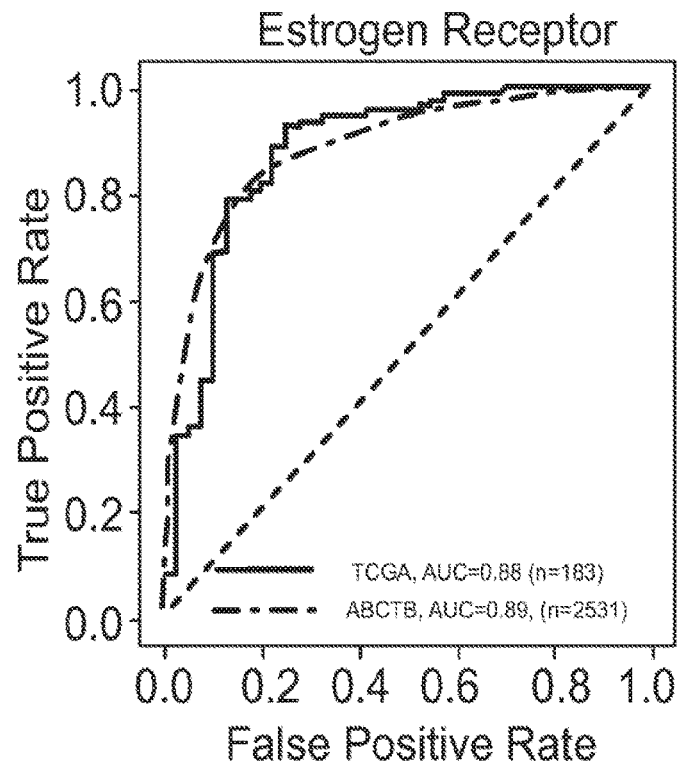
Figures 2, 7B:
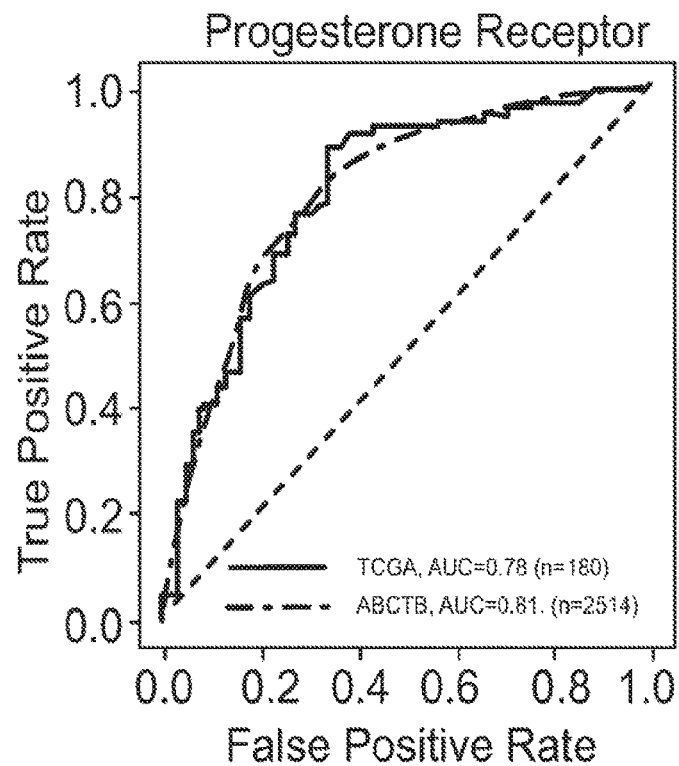

As set forth below in more detail, tissue fingerprints are implemented by training a neutral network to fingerprint pathologic tumor samples from a training set and then tested it on a simple matching task using tumor images from new patients. Briefly, multiple images were divided into halves, and a network attempted to learn a vector of features (a "fingerprint") that could correctly pair the halves (FIG. 1). An important aspect of this work was using the matching task to learn stain- and site-invariant features of the architecture. We controlled for these sources of noise by testing whether the fingerprints could match tissues from the same patients that had been stained and scanned at different sites. Optimizing on the task of matching, we performed experiments testing the impact of training set size and methods of image normalization. The features (fingerprints) were extracted from the pre-wired fingerprint network after training internship was accomplished and used to classify between groups of tumors with biologically relevant molecular pathway annotations.[12,13]

Figure 1B:
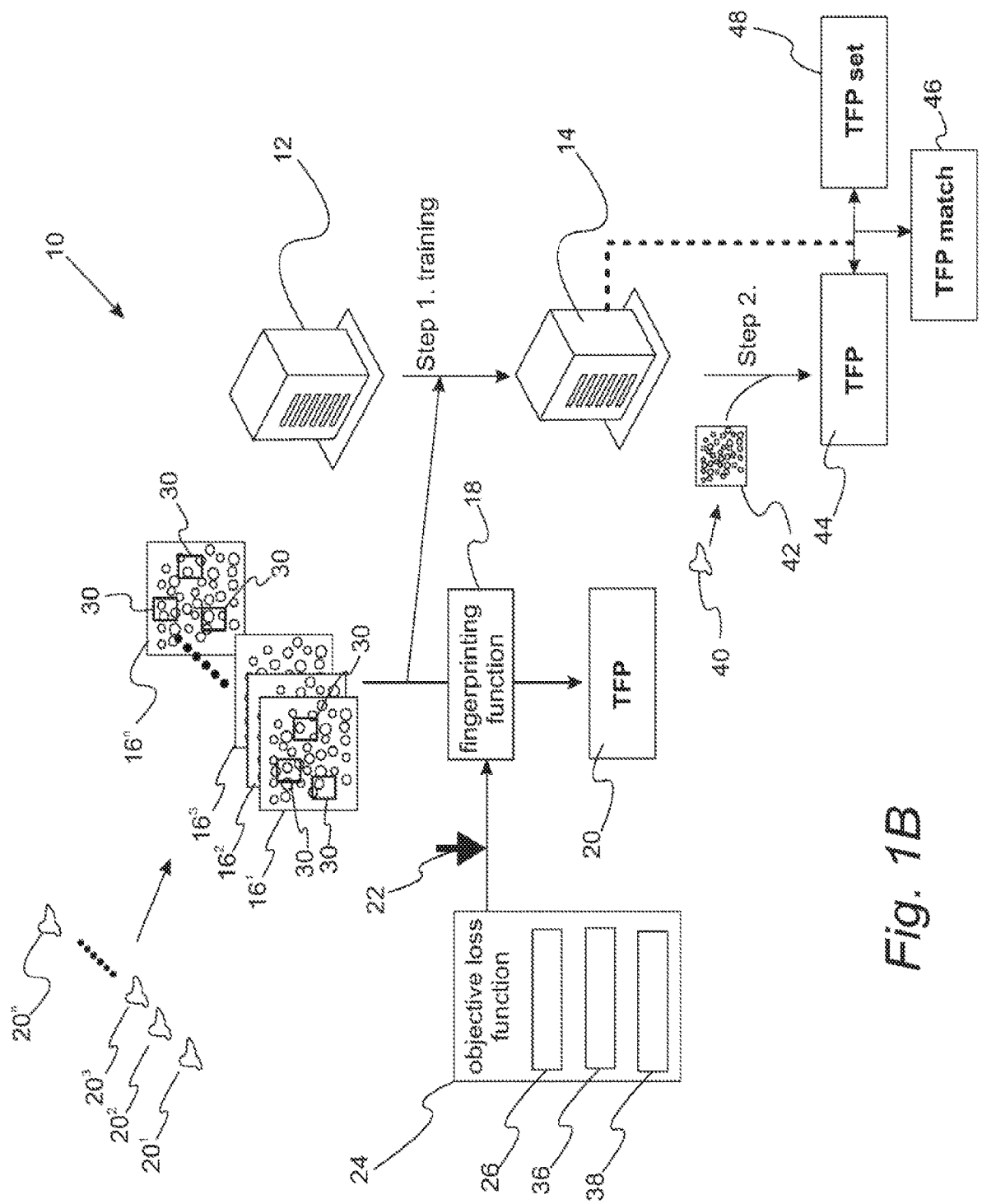
FIG. 1B. Schematic of a histopathology classification method using tissue fingerprints.
Figure 1C:
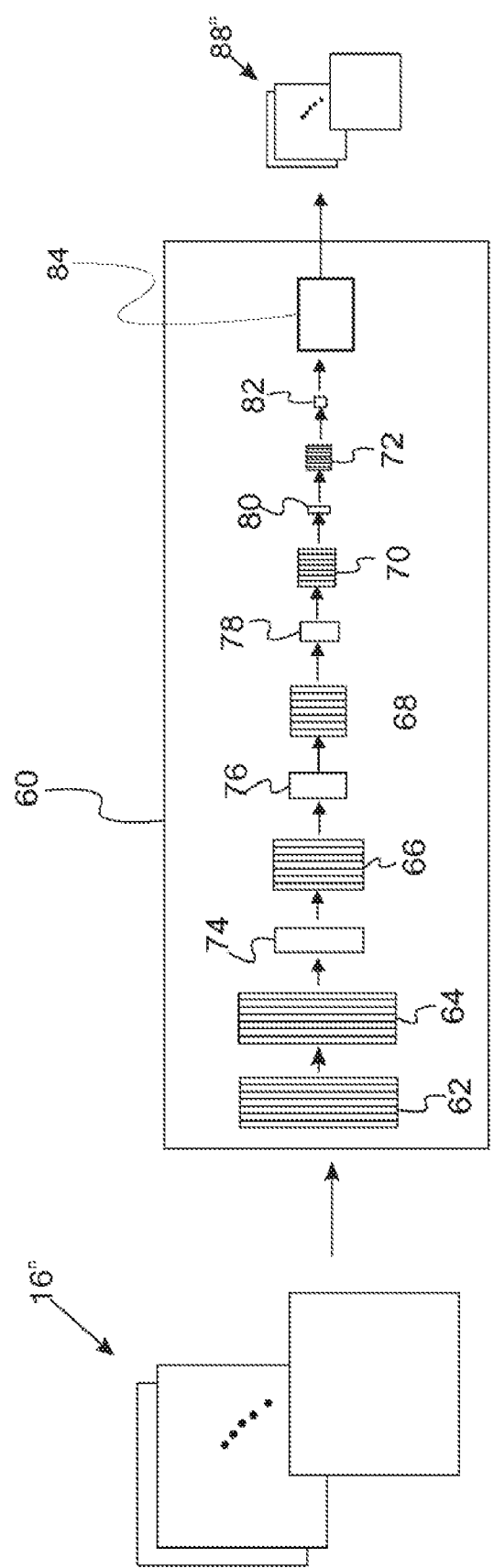
FIG. 1C. Schematic of a convolutional neural network used in the method depicted in FIGS. 1A and 1B.

With reference to FIGS. 1A, 1B, and 1C, a histopathology classification method through machine self-learning of "tissue fingerprints" is illustrated. Characteristically, the histopathology classification method is implemented in a digital medium environment. FIG. 1A shows that in general, the method includes a first step of training a neural network to learn the tissue fingerprints and a second step of applying the fingerprint to a clinical task. FIG. 1B provides a more detailed schematic of the method. With reference to FIGS. 1A and 1B, histopathology classification method 10 includes a step of training an untrained machine learning device 12 executing a neural network (i.e., computer instructions for a neural network) to form a trained machine learning device 14. The training step is accomplished by receiving a digital image 16' of a histologic sample as input to a tissue fingerprinting function 18 and outputting a vector of numbers called a tissue fingerprint (TFP) 20 that describes histologic patterns within the digital image. The untrained machine learning device 12 is trained with digital images $16^n$ from a plurality of characterized or uncharacterized stained tissue samples $20^p$ where n is an integer equal to the number of digital images and p is the number of tissue samples. The number n of digital images and the number p of characterized or uncharacterized stained tissues samples $20^p$ can independently be from 10 to several hundred or more. The untrained machine learning device 12 learns the tissue fingerprinting function 16 through an optimization procedure 22 that minimizes an objective loss function 24. Details of the object loss functions are set forth below in the experimental section. The objective loss function 24 includes a first component 26 promoting the learning of the tissue fingerprinting function that can be used to match digital image patches 30 from the same sample but distinguish digital image patches 32 from multiple samples. The objective loss function 18 also includes an optional second component 36 that promotes learning of the tissue fingerprinting function 18 that is invariant to sources of pathology artifacts that are encountered during tissue processing. Examples of such artifacts include, but are not limited to, pathology artifacts that include variation in tissue stain concentrations, in tissue processing procedures, differences in slide scanning equipment, and combinations thereof. In a refinement, multiple tissue fingerprints across different tissue regions are used in a pooled fashion to determine tissue status. It should also be appreciated that samples are derived from (i.e., obtained from) sub-regions of tissue within whole slide images from either a tissue blocks or core biopsy specimens. In a refinement, the objection loss function further includes a third optional component 38 to apply an image normalization step before training.

The method also includes a step 2 of predicting the status of a stained tissue sample 40 of unknown status. This step is accomplished by obtaining a sample digital image 42 for a stained tissue sample of unknown status 40. The trained machine learning device 14 is applied to the sample digital image to determine a predicted tissue fingerprint 44 for the stained tissue sample 40 of unknown status. Finally, a best match 46 of the predicted tissue fingerprint to a set 48 of tissue fingerprints for samples of known status is found.

In another refinement, a relationship between a collection of characterized samples and their fingerprints is learned and then applied to predict a status for the stained tissue sample of unknown status.

In a variation, learning of a tissue fingerprinting function 18 that is invariant is promoted by obtaining paired images 50 and penalizing the optimization procedure for learning a fingerprint function that assigns different fingerprints to the paired images. Typically, the paired images 50 can be obtained either by sectioning a tissue sample that is processed at different laboratories, or by altering pixels of an original image to give an appearance of having been processed at a different laboratory.

In another variation, a relationship is learned between the tissue fingerprint and a diagnostic, prognostic, or theragnostic data annotation of the sample. From these features, a therapeutic treatment strategy can be determined for a subject from a subject's predicted status for the status of a diagnostic feature with which the subject is subsequently treated. In a refinement, the subject is treated with a cancer therapeutic agent.

In another variation, the diagnostic, prognostic, or theragnostic feature, is the presence or absence of a biomarker. Typically, in this variation, the stained tissue sample of unknown status is a cancer sample. Such a cancer sample may be a cancer of unknown origin, such as cancer from a metastatic site. In a refinement, the tissue fingerprinting function is used to infer the site from which the cancer originated (tissue of origin of the cancer). Examples of useful biomarkers include, but are not limited to, estrogen receptor (ER), human epidermal growth factor receptor-2 (HER2), progesterone receptor (PR), proliferation marker Ki-67, and cytokeratin markers. When the biomarker is ER, a predicted status can be used to determine specific treatments. In a refinement, the biomarker is ER, PR, and HER2 with a predicted status indicating prognosis.

As set forth above, the untrained machine learning device 12 (and therefore, untrained machine learning device 1) is a computing device (e.g., a computer) executing instructions for the neural network. Typically, the neural network is a convolutional neural network. In this regard, the convolutional neural network includes a plurality of convolutional layers and a plurality of pooling layers. FIG. 1C provides an idealized schematic illustration of a convolutional neural network executed by untrained machine learning device 12. Typically, the neural network is a convolutional neural network. In this regard, the convolutional neural. It should be appreciated that any deep convolutional neural network that operates on the pre-processed input can be utilized. The convolutional network can include convolutional layers, pooling layers, fully connected layers, normalization layers, a global mean layer, and a batch-normalization layer. Convolutional neural network layers can be characterized by sparse connectivity where each node in a convolutional layer receives input from only a subset of the nodes in the next lowest neural network layer. The Convolutional neural network layers can have nodes that may or may not share weights with other nodes. In contrast, nodes in fully-connected layers receive input from each node in the next lowest neural network layer. For both convolutional layer and fully connected layers, each node calculated its output activation from its inputs, weight, and an optional bias. During training, optimal values for the weight and bias are determined. For example, convolutional neural network 60 receives a plurality of digital images 16″ which are processed as set forth above. Convolutional neural network 60 includes convolution layers 62, 64, 66, 68, 70, and 72 as well as pooling layers 74, 76, 78, 80 and 82, optional processing layer(s) 84, and multiple outputs 88″ (where n is as above). The pooling layers can be max pooling layer or a mean pooling layer. Each of the convolution layer can include multiple internal feature maps which can change from layer to layer via subsampling and convolution. The present embodiment is not limited to by the number of convolutional layers, pooling layers, fully connected layers, normalization layers, and sublayers therein.

Figure 2:
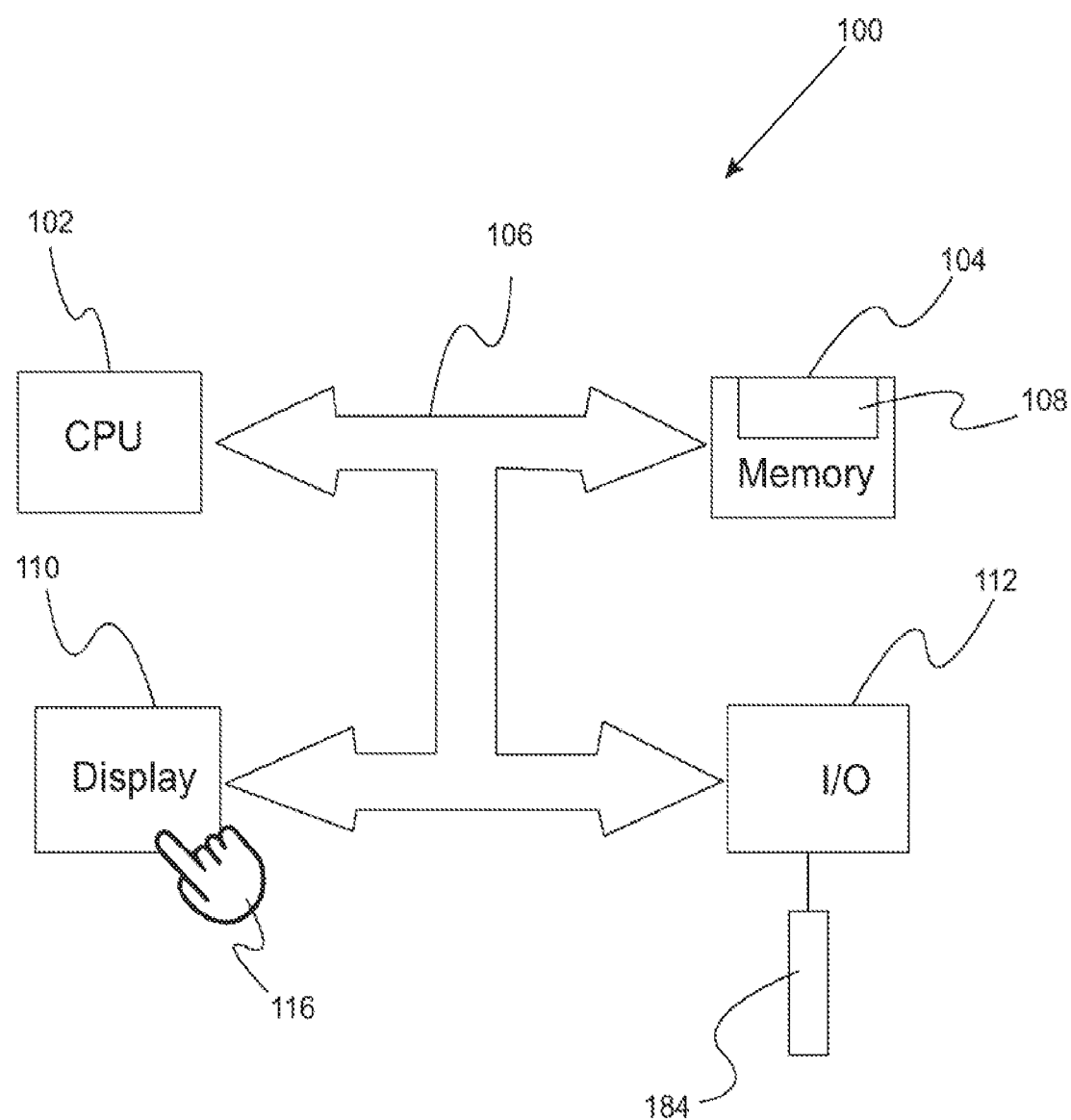
FIG. 2. Schematic of a computing device for implementing the machine learning method set forth herein.

As set forth above, the histopathology classification methods are implemented by a computing device. In general, computing devices are computer processor-based electronic devices. With reference to FIG. 2, computing device 100 includes computer processor 102 that executes the instructions for authoring the chemical mechanism problem or solving it. It should be appreciated that virtually any type of computer processor may be used, including microprocessors, multi-core processors, and the like. The instructions for the method typically are stored in computer memory 104 and accessed by computer processor 102 via connection system 106. In a variation, connection system 106 is and/or includes a data bus. In a refinement, computer memory 104 includes a computer-readable medium 108 which can be any non-transitory (e.g., tangible) medium that participates in providing data that may be read by a computer. Specific examples for computer memory 104 include, but are not limited to, random access memory (RAM), read-only memory (ROM), hard drives, optical drives, removable media (e.g., compact disks (CDs), DVD, flash drives, memory cards, etc.), and the like, and combinations thereof. In another refinement, computer processor 102 receives instructions from computer memory 104 and executes these instructions, thereby performing one or more processes, including one or more of the processes described herein. Computer-executable instructions may be compiled or interpreted from computer programs created using a variety of programming languages and/or technologies including, without limitation, and either alone or in combination, Java, C, C++, C#, Fortran, Pascal, Visual Basic, Java Script, Perl, PL/SQL, etc. Display 110 is also in communication with computer processor 102 via connection system 176. Computer device 170 also includes various in/out ports 112 through which data from a pointing device 114 may be accessed by computer processor 102. Examples for the computing device include, but are not limited to, desktop computers, laptops, or servers. Examples of pointing devices include a mouse, touch screen, stylus, trackball, joystick or touchpad. In a particularly useful variation, the pointing device is incorporated into display 108 as a touch screen by which user 116 interacts with a finger. In a variation, a non-transitory storage medium or media (hard drives, optical drives, removable media (e.g., compact disks (CDs), DVD, flash drives, memory cards, etc.) has encoded thereon instructions for the steps executed by computer processor 102 in performing the steps of the methods set forth herein.

The following examples illustrate the various embodiments of the present invention. Those skilled in the art will recognize many variations that are within the spirit of the present invention and scope of the claims. It should be appreciated that the techniques set forth below can analogously be applied to the other biomarkers set forth above.

Methods

Tissue Fingerprinting

Dataset

Figures 3, 7B:
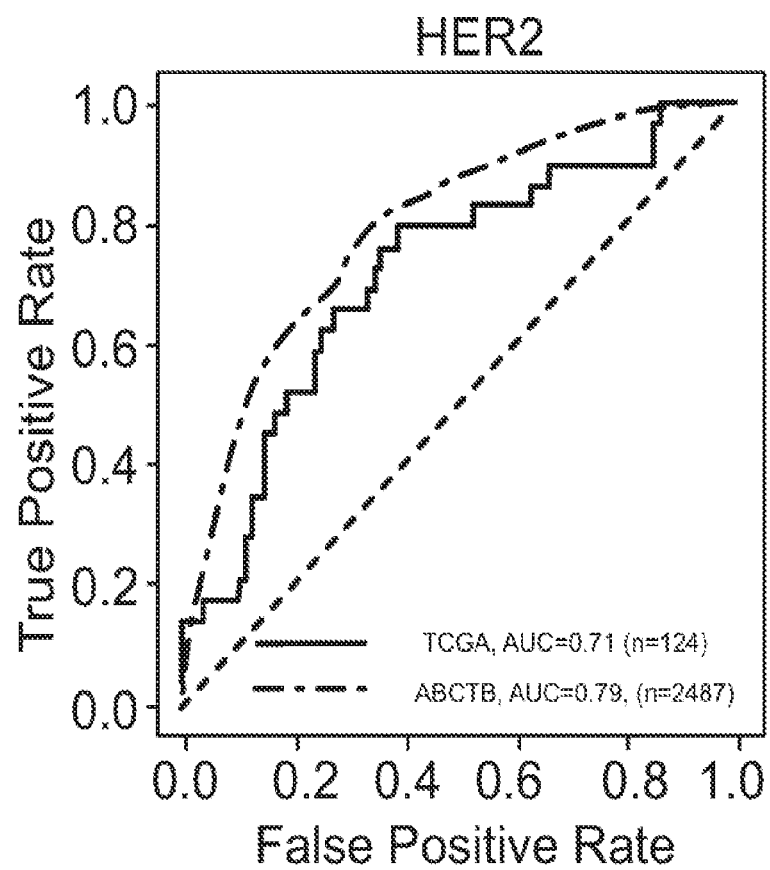

The tissue fingerprint network was trained on images of tissue microarray (TMA) cores. The tissue microarrays (TMAs) used in this study were obtained from supplier US Biomax, Inc. Array BR20823, containing 207 tissue cores from 104 patients, was used to train the fingerprint network. Array BR20819, containing 208 cores from a separate group of 104 patients, was used to test the trained model. One or two sections were obtained from each array (for BR20823 and BR20819, respectively), which were H&E stained using standard laboratory protocols, before scanning was performed at 40× resolution (0.249 microns per pixel) on a Carl Zeiss slide scanner. US Biomax, Inc. kindly provided images of serial sections of these microarrays that had been stained and scanned by their protocols on an Aperio slide scanner at lower resolution (0.49 microns per pixel). Additional breast cancer tissue images were used to increase the size of the training set for experiments 2 and 4. These images are of breast cancer tissue from a variety of sources having distinct patients from BR20819 and BR20823. (see, Table 1 in FIG. 3)

Neural Network Training (Experiments 1 and 2)

Neural networks were trained and run on NVIDIA P100 GPUs (Oracle Cloud Infrastructure BM.GPU2.2 instances). The fingerprint network was trained on image patches randomly extracted from the BR20823 images. Each circular tissue core was isolated, scaled to 0.5 micron/pixel resolution (bilinear resampling), and cropped to a 1600× 1600 pixel square. These squares were assigned a numeric index from 1 to 207, reflecting their position on the array. Each square was then divided into left and right halves. During training, a small image patch (224×224 px) was sampled from the left half, augmented through rotation, color spectrum augmentation[1], color normalization.[6] It was then passed to a neural network trained to minimize cross entropy loss (i.e., an example of an objective loss function) between patient identity and a predicted index. During training, progress was monitored by measuring how well the network could predict the core index from patches from the right halves of the tissue images, which it hadn't seen. When this accuracy plateaued, training was stopped and the quality of the features on the tissue matching game was tested. Experiments 3 and 4 used the more complex objective loss function described below.

In the four experiments described, the standard implementation of the Resnet34 architecture[15] provided by the PyTorch library[16] was used. The network was randomly initialized and trained from scratch. Additionally, larger networks, including Resnet50 and Resnet100, were trained using the conditions of experiment 4, but found the same performance as Resnet34 (results not shown). The benefit of larger networks may depend on the size of the training dataset. Here the concept of fingerprinting with a relatively small dataset is demonstrated, but training on larger datasets may demonstrate added benefits of deeper networks.

Figure 4:
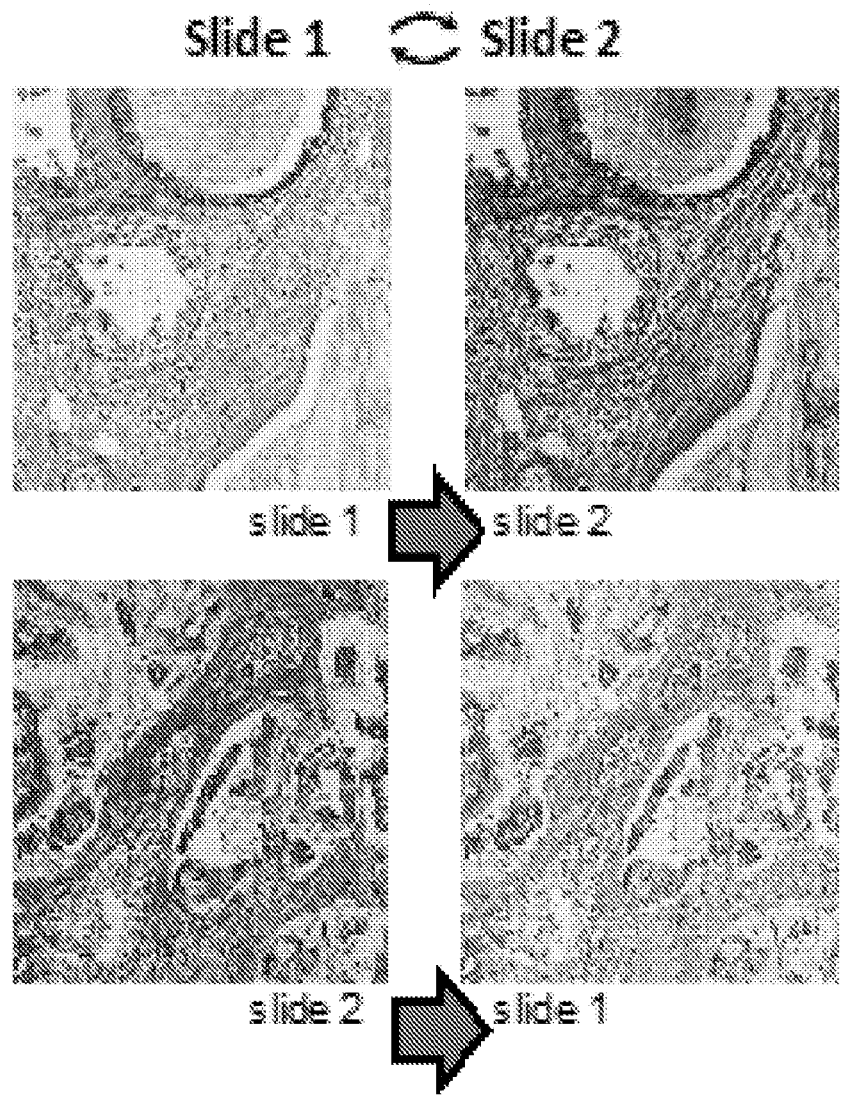
FIG. 4. CycleGAN normalizes the staining colors and styles of tissue images while preserving morphology. Top: the style of slide 1 is translated into the style of slide 2. Bottom: the style of slide 2 is translated into the style of slide 1.

Promoting Style Invariance by GAN-Based Style Transfer (Experiments 3 and 4):

Neural style transfer was performed offline using Cycle-GAN[17], a method of neural style transfer, that aims to alter the style of images while preserving fine details. Briefly, the CycleGAN approach consists of training two neural nets, a generator which takes an image A transforms it into an image of style B, and a discriminator which is trained to distinguish between generated images and real ones. The networks are trained simultaneously as adversaries. As the discriminator improves, the generator is challenged to learn better transformations from style A to B. Conversely, as the generator improves, the discriminator is challenged to learn better features that distinguish real and generated images. In this project, the open-source CycleGAN code was used without modification. The network was trained to transfer styles between images of BR20823 that were stained by the array manufacturer (US Biomax) or at our site (style transfer between slides 1 and 2, respectively, as shown in FIG. 4). Thus, the original set of 13,415 cores was augmented to three-fold its original size via neural style transfer (each core has an original image, a virtual USC stain and a virtual Biomax stain). Following style transfer, the objective loss function to promote style invariance was adapted. The new objective loss function has two components, a cross entropy loss (abbreviated 'CE') to predict the identity of each patch, which was the loss term used in experiments 1 and 2, plus an additional loss term to minimize the distance of fingerprints from different styles. The additional loss term is the squared error (abbreviated 'SE') between the L2-normalized fingerprints, where a fingerprint is the 512-dimensional (512D) feature vector from the last layer of the Resnet.

Loss is defined for a pair of images from tissue core$_i$ (1≤i≤207): Image$_{i1}$, and Image$_{i2}$. Image$_{i2}$ is a re-styled version of Image$_{i1}$ that contains the same morphological information. The loss is a sum of two cross entropy losses and a fingerprint distance loss. The symbol, γ, is a constant. In our experiments, we used γ=0.5.

Cross entropy is defined using the classification vector produced from the network for each image. This vector contains 207 elements. Images, from core; produces a classification vector $c_{iX}$.

$$CE(Image_{ix}, y = i) = -\ln\left(\frac{e^{c_{ix}[y]}}{\sum_z e^{c_{ix}[z]}}\right)$$

Fingerprint distance loss is defined using the fingerprints produced by the neural network for each of the images. If the fingerprints for Image$_{i1}$, and Image$_{i2}$ are called FP$_{i1}$ and FP$_{i2}$, fingerprint distance loss is the following. ‖ ‖ and SE refer to the L2 norm and the Euclidean distance, respectively.

$$d_{FP}^2(Image_{i1}, Image_{i2}) = SE\left(\frac{FP_{i1}}{\|FP_{i1}\| + \epsilon} + \frac{FP_{i2}}{\|FP_{i2}\| + \epsilon}\right)$$

Creating Beat Maps of Recognized Regions

Heat maps of tissue cores showing the parts of an image most predictive of tumor identity (FIG. 6) were generated. The region colors were determined as follows: each core image was divided into overlapping square patches (size 224×224 pixels, with 80% linear overlap). Each patch was passed to the neural network, and a probability vector was calculated predicting the identity of each core via Softmax. Since there are multiple cores per patient, the 207 probabilities were aggregated into 104 probabilities (one per patient) by summing the probabilities of cores that came from the same patient. Each heat map shows the probability of predicting the correct patient and is shaded from 0 (blue-light) to 1 (red-dark).

Stain Normalization is Necessary for Fingerprinting

Four experiments were performed, varying training set size and image normalization, to determine how to best train a fingerprint network (Table 2). It is hypothesized that training on large numbers of cores would improve accuracy, and that image color normalization would greatly improve training on small data but have a smaller effect on larger datasets. In experiment 1, the 207 tissue cores were collected from slides 1 and 2 (serial sections of the training TMA that were stained by the supplier and USC, respectively), divided them in half, and trained the network to recognize patients based on patterns in one of the halves. (It was arbitrarily chosen to train on the left halves). Each core was assigned a number from 1 to 207, and the network was trained to identify the number from a patch sampled from the image-half. In experiment 2, the dataset was scaled over 20-fold: adding 13,000 additional training images. Again, the network was trained to predict the index. In experiments 3 and 4, the same datasets were used as before, but included a color normalization procedure based on neural style transfer.[17,20] In the first two experiments, it was predicted that as the network was trained to recognize increasing numbers of images, it would automatically learn stain-invariant features. In the second two experiments, the style transfer algorithm CycleGAN[17] was used to recolor images (FIG. 4), making them appear as if they were prepared at a different site. CycleGAN can exchange the texture between two spatially similar image sets, while preserving overall structural information. Compelling examples include transforming photographs into impressionist paintings and horses into zebras. Here, we use CycleGAN to transfer the H&E staining coloration from a reference site to images from other sites. Then we trained the networks to look at both images and predict the same features, cancelling out the effect of stain variation.

TABLE 2

Fingerprinting Results

| # | Description | Dataset Size N. Training Cores (N. Patients) | Neural Style Transfer | Network | # Test Cores | CV Acc. | Test Core Acc. | Test Patient Acc. |
|---|---|---|---|---|---|---|---|---|
| 1 | Small Dataset/ No Style Transfer | 414 (104 | – | Resnet 34 | 208 | 77% | 22% | — |
| 2 | Large Dataset/ No Style Transfer | 13415 (3302) | – | Resnet 34 | 208 | 77% | 26% | — |
| 3 | Small Dataset/ Style Transfer | 414 (104) | + | Resnet 34 | 208 | 93% | 43%. | — |
| 4 | Large Dataset/ Style Transfer | 13415 (3302) | + | Resnet 34 | 208 | 95% | 63% | 93% |

ER, PR, Her2 Classification from Whole Slides Datasets

The whole slide images used in this study were obtained from The Cancer Genome Atlas[12] (TCGA) and the Australian Breast Cancer Tissue Bank[13] (ABCTB). We included 939 cases Breast Carcinoma from TCGA and 2531 Breast Cancer cases from the ABCTB. Clinical characteristics are summarized in Table 3. Of note, molecular status of ER, PR, and Her2 was assessed clinically, where annotations were made on the patient level.

TABLE 3

Clinical characteristics of breast cancer patients

| Breast Cancer Cohort | TCGA | ABCTB |
|---|---|---|
| Number of Patients | 939 | 2531 |
| ER-positive | 723 | 2007 |
| ER-negative | 216 | 524 |
| PR-positive | 623 | 1798 |
| PR-negative | 311 | 716 |
| Her2-positive | 151 | 371 |
| Her2-negative | 508 | 2116 |
| Age (years) | | |
| min | 26 | |
| mean | 58.2 | |
| max | 90 | |
| Stage | | |
| I | 156 | |
| II | 539 | |
| III | 210 | |
| IV | 16 | |
| Histologic Grade | | |
| Grade 1 | | 364 |
| Grade 2 | | 904 |
| Grade 3 | | 1004 |
| Tumor Size | | |
| T1 | 234 | |
| T2 | 546 | |
| T3 | 123 | |
| T4 | 34 | |
| Node Status | | |
| N0 | 443 | |
| NI | 315 | |
| N2 | 100 | |
| N3 | 65 | |
| node negative | 443 | 1143 |
| >1 node positive | 480 | 1388 |
| Metastasis Status | | |
| M0 | 785 | |
| M1 | 18 | |

Training a Patch-Based ER,PR,Her2 Classifiers Directly Front Images (Control)

Similar to other deep learning approaches, a patch-based classifier was trained to predict molecular marker status. All experiments were conducted using five-fold cross validation. First, each whole slide image was grossly segmented into foreground vs. background. The foreground areas were divided into non-overlapping squares of (112×112 microns), which were scaled to a final patch size of 224×224 pixels. 120 patches per patient were randomly selected and used for downstream analysis. To train the classifier, the entire set of TCGA patients was split into five groups. For each cross validation fold, three groups were used to train, one group (the "overfitting group") was used to monitor overfitting and perform early stopping, and the remaining group was used to test the network's final performance. To the train the network, patches were assigned a binary label per the patient-level annotation, but early stopping was implemented by averaging the predictions of all patches belonging to overfitting group and measuring the patient-level AUC (area under the ROC curve) score. These experiments used a standard implementation of Resnet34.

Training ER, PR, Her2 Classifiers Directly from Fingerprints

Using the same image patches and cross validation splits from the control experiment (described above) and the previously trained fingerprint network, 512D fingerprints were extracted for each image patch and then trained a second "biomarker" neural network to predict marker status based on these fingerprints. The second network has the following structure: input, 512×8 linear layer, rectified linear unit nonlinearity, 8×1 linear layer, hyperbolic tangent nonlinearity. The parameters of this network were trained in batches consistent with multiple instance learning (see Training the fingerprint-based classifier to predict molecular markers). Similar to the control experiment, multiple patch predictions were pooled to make patient-level predictions, and the reported ROC curves compare patient-level score and clinical marker status. As a control for the features, the same workflow using image features extracted from a Resnet34 network pretrained on the ImageNet dataset was implemented. The parameters for this model were obtained from the Torchvision Python library.

Training the Fingerprint-Based Classifier to Predict Molecular Markers

The classifier for each molecular marker was trained in the following manner. From the training set, 120 patches were extracted per patient (as set forth above), and fingerprints were extracted using the pre-trained fingerprint network. Then, a matrix containing these fingerprints was created and loaded into memory. The dimensions of the matrix were (N×120×512), where N corresponds to the number of patients in the training set. The tensor was reshaped into a data matrix "Xtrain," with the following dimensions (N*120×512) Additionally a "ground truth' vector {length=N} containing the ground truth data for the training patients was prepared. Each value in the vector signifies positive or negative biomarker status by the value of +1 or −1 Xtrain was passed to a neural network with the following structure:
  Linear (512, 8)
  ReLU
  Linear (8, 1)
  Tan h
The output of the network after receiving Xtrain is of size (N*120, 1) and is labeled "Pred_unscaled" The matrix, "Pred_unscaled' is reshaped to size: N×120 Each row in the matrix is normalized as follows:
  The absolute value is taken of Pred_unscaled and summed over the horizontal dimension, producing a "weight' vector of length N
  Each row in Pred_unscaled is divided by the corresponding weight vector, producing a matrix Pred_scaled of shape (N×120)
    For each row i (0 . . . N):
      Pred_scaled[i]=Pred_unscaled[i] weight[i]
  The output is a matrix of shape N×120
  Each row in the matrix Prod_scaled is summed to produce a 1D "prediction" vector for the training dataset of length N. The loss is calculated by the binary cross entropy between the prediction vector and the ground truth vector. The weights of the model are updated using back propagation and gradient decent. We used the Pytorch implementation of the Adam optimizer with learning rate of 0.0001 Training was continued until the loss on the cross-validation set stopped decreasing as per the methods section. The motivation for applying the normalization step using the average of the absolute value was to allow the network to pay attention to certain areas and ignore others. The Tan h nonlinearity outputs a score from −1 to 1. Areas predicted to be 0 are not contributory to the weight and hence do not factor into the final score for the slide. However, areas that are strongly positive or negative affect the weighting and influence the final patient prediction.

External Validation of the Whole-Slide ER, PR, or Her2 Classifier

After the five-fold cross validation experiments on the TCGA dataset, the classifier was validated on an independent test set from the ABCTB. These images were processed like those from TCGA: 120 patches (112×112 microns, resized to 224×224 pixels) were extracted per patient, and fingerprints were calculated using the pre-trained fingerprint network. The TCGA-trained biomarker network was then used to predict marker status of patients in the ABCTB dataset. An AUC score was calculated from the ROC curve comparing the neural network predictions to clinical status from the ABCTB.

Visualization of Regions Used to Predict Clinical ER Score Generating Heatmaps of Predicted ER Status Given the high AUC for the ER classifier, heatmaps showing the regions predicted to be highly ER-positive or negative across whole slides were made. Every very non-overlapping foreground patch (112×112 micron) were extracted from TCGA WSIs and compressed them into a 512D fingerprints using the pretrained fingerprint network. Subsequently, the pre-trained ER network was used to make patch-level predictions across the entire slide. The predictions are shaded in grayscale. Black signifies a prediction of −1 (ER-negative), while white signifies +1 (ER-positive). Gray values correspond to scores close to 0 (indeterminate). All visualizations of ER predictions and features show the validation and test sets of one cross-validation split. Hence, none of the data reflect images that were used to update the values of the weights.

Heatmaps of Tissue Types

TCGA whole slides were segmented into background, epithelium, stroma, and fat by training a patch-based classifier on a publicly available dataset of WSIs with tissue type annotations.[18] The segmentations were subsequently assessed for gross accuracy at 2× resolution, and a small portion of heatmaps (<5%) were manually corrected.

Visualizing the tSNE Embedding of WSI Fingerprints

An efficient implementation of the tSNE algorithm was used to plot a 2D manifold of the fingerprints.[19] Each point represents one fingerprint, which corresponds to a single patch from a WSI. The color of the point represents the ER prediction, which is shaded from blue (−1, ER negative) to green (0, neutral) to red (+1, ER positive). Grossly, the presence of regions containing a predominance of blue or red points was appreciated. To assess the visual similarity of patches in these clusters, 12 cluster centers were manually selected and five patches closest to these centers visualized.

Results

In summary, the basic aim of the present invention was to develop a biologically meaningful set of H&E histologic features. It is hypothesized that in the process of training a neural network to "match two halves" of tissue cores, it would learn a compact, but meaningful representation of tissue architecture. Following training of the fingerprint network, which was influenced by the discovery of the importance of stain-normalization, various methods of predicting molecular marker status from whole slides were compared. It was found that a fingerprint-based approach out-performed traditional transfer-learning and direct patch-based classification. Moreover, fingerprint-based classifiers continued to perform well on an independent, external dataset. When the fingerprint-based classifier was applied to a small collection of slides in the test-set, it was found that they produced interpretable heatmaps, and predominantly focus on epithelial patterns to make predictions.

Learning Fingerprints

The networks were trained to learn fingerprints from tissue cores in TMAs. The TMA format makes it easy to process one set of tissues in multiple ways and allowed us to simulate the batch-effects that are commonly encountered at pathology labs. By staining and scanning one section at USC and another stained by the TMA supplier (US Biomax), we obtained paired images with the same architectural features, but different coloration. Our goal was to learn a fingerprint that summarized the architecture but ignored the staining differences.

We used one TMA to train (BR20823) and another TMA to test (BR20819, Table 1). Each TMA contains approximately 208 tissue cores from 104 patients, with no patient overlap between arrays. We used 3 serial sections of the training TMA. One section was stained/scanned by the TMA supplier (slide 1), the other two were stained at USC (slides 2, 3). Two serial sections of the test array were similarly collected, stained at USC and by the TMA supplier (slides 4 and 5).

To compare the quality of the fingerprints learned in the four experiments, tissue matching on the test TMA sections was performed. Using the thus-trained NN, we calculated fingerprints for left halves of cores from one section (stained by the array manufacturer, slide 4) and the right halves from the other (stained at USC, slide 5), and matched each left fingerprint to the nearest right fingerprint in 512D fingerprint space. Since there were 208 cores in the test set, we report a core-level accuracy (acc.=number of cores matched correctly/208). The null accuracy by chance is 0.4% (1/208 cores).

While fingerprints from all four experiments matched cores better than chance, the accuracy was highest in experiment 4, which used a large training set with stain normalization. The fingerprints from this method matched cores with 63% accuracy (131/208 cores). Surprisingly, stain normalization seems to be necessary to get the performance gains of larger training sets. Comparing the results of experiments 2 and 3 to the baseline, increasing training set size in the absence of stain-normalization (experiment 2) provided only a miniscule improvement in matching accuracy over the baseline. However, stain-normalization nearly doubled the accuracy. It's important to note that in all four experiments we used standard image augmentation during training. Immediately before the image was shown to the fingerprint network, it was randomly adjusted for brightness and contrast and converted to grayscale. Even with these procedures, which were intended to make networks invariant to color differences between images,[6] doing an additional style normalization step before the augmentation provided a significant improvement.

When we examined the mistakes from the network in experiment 4, it was noticed that a large portion of them were due to an aspect of the study design, using a test set with 2 cores per patient. Several of the misclassified cores were incorrect at the core level but correct at the patient level. This is because some tumors are morphologically homogeneous and have similar patterns across cores. Thus, we also calculated a pooled accuracy, which uses the fingerprints from both left cores to match both right cores and found that fingerprints could match patients with 93% accuracy (see methods for details).

Encouraged by the high patient-level accuracy of the matching, the features of the final neural network layer was studied. When the network is shown an image, this layer produces a 512D vector of real numbers, the tissue fingerprint. In the remainder of the work, the network was applied to extract fingerprints and explore how they can be used to link histologic patterns to clinical subgroups of breast cancer.

Fingerprint Visualizations Reveal Style-Invariant Histologic Patterns

Figure 5A:
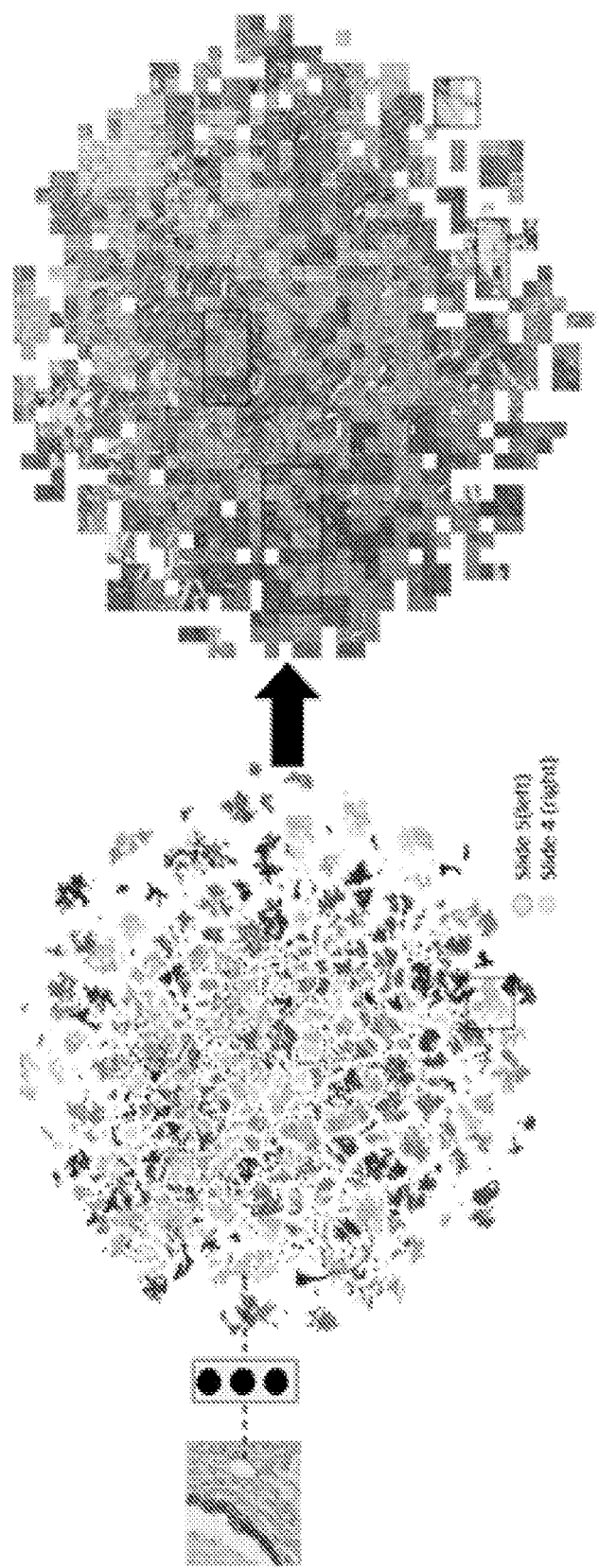
FIGS. 5A, 5B, and 5C. A: Representative tSNE visualization of fingerprints from the test set. In this visualization, left halves from slide 5 and right halves of slide 4. B: Visualization of a representative pair. Left half presented on top, right half on the bottom, the middle shows a heat map of fingerprint distance (distance from fingerprints from the bottom image to the average fingerprint of the top image). C: Left, exploded displays of the original patches in the embedding show similar histologic features (nucleoli, micro-papillae, fat, mucin).

As both a control and as a starting point for understanding the features in the fingerprints, we performed two-dimensional fingerprint visualization. The left and right halves of cores were taken from the test slides, which had been stained at different sites, and calculated fingerprints for patches from the halves. Next, the fingerprints were embedded in a tSNE plot (FIG. 5A). tSNE is a technique that compresses high dimensional vectors into a 2D space while preserving local structures in the data.[21] Its primary utility in this work is to approximate the relationships within a high dimensional space and make them accessible for visual analysis. After using tSNE to compress the fingerprints into 2D coordinates and plotting each coordinate as a point colored by patient index, it was observed that the left and right halves from the same patient are close in the embedding space. Since points that are nearby on a tSNE plot also tend to be nearby in the original space, this visualization provides evidence that fingerprints of similar tissues are similar in spite of differences in staining. Moreover, visualizing the same embedding as a map of image patches, instead of colored points, reveals that different regions of the map contain different architectures, such as nucleoli, fat, micropapillary growth, and mucin patterns (FIG. 5C). Thus, in the embedding space, fingerprints are clustered by histologic patterns even if the patches they come from exhibit markedly different colorations and styles.

Fingerprints can be Used to Visualize Similar Regions Between Tissues

Figure 5B:
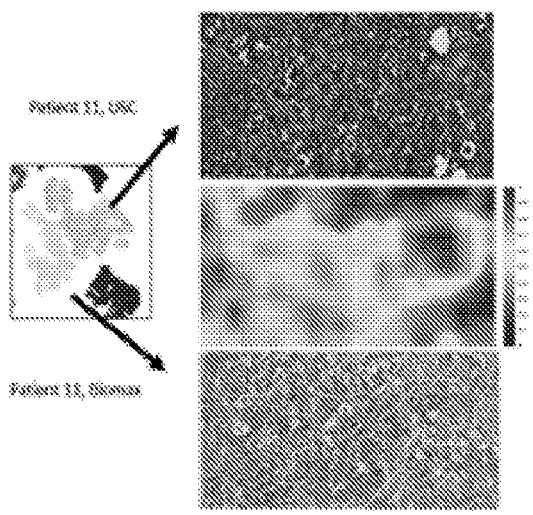
Figure 5C:
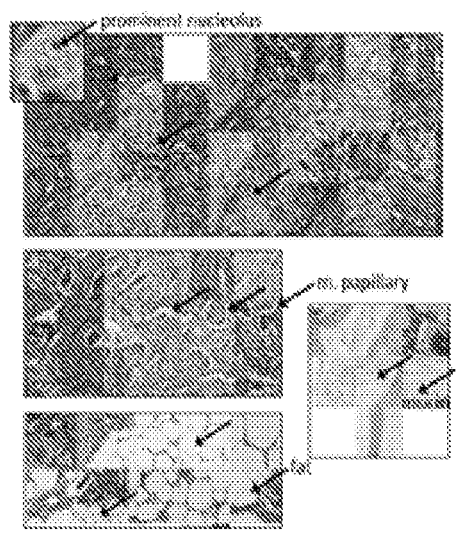

FIG. 5B focuses on a specific Left/Right pair from the test set. The average fingerprint of the right half is calculated and a heat map plotted showing the similarity (defined as 1−normalized Euclidean distance) from each patch in the left half to the average fingerprint of the right half (red is similar, blue is dissimilar). The overlay (bottom) shows that similarity between the right and left halves is highest in a discrete region that appears to contain epithelial cells. This observation is consistent with the abundance of epithelial cells in the right image, suggesting that fingerprint similarity may have utility in histologic search.

Fingerprints Combine Epithelium and Stromal Features

Figure 6A:
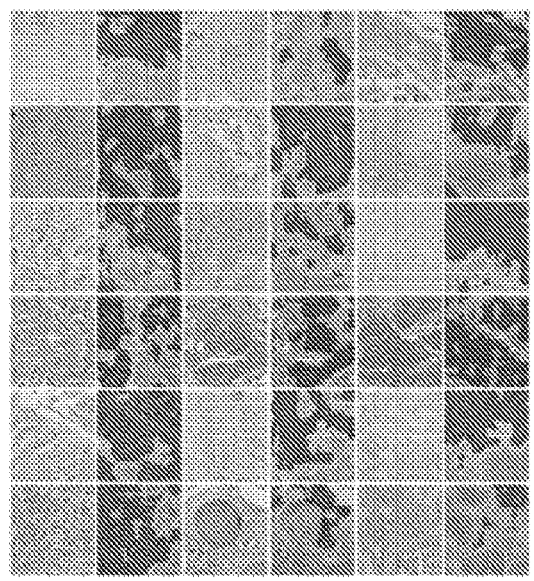
FIGS. 6A, 6B, and 6C. A: heat maps of areas that lead to accurate patient classification. Higher probability regions (red) are more predictive of patient identity, and hence distinctive, than blue regions. B: an exploded view of two cores from (A). C: Legend FIG. 7A. Illustration of whole slide clinical ER classification. An analogous procedure was used for PR and Her2 classification. Fingerprints were extracted from 120 random image patches, and a second ER-classifier, acting on the fingerprints, made local predictions, which were averaged to produce a continuous whole-slide-level ER-score.
Figure 6B:
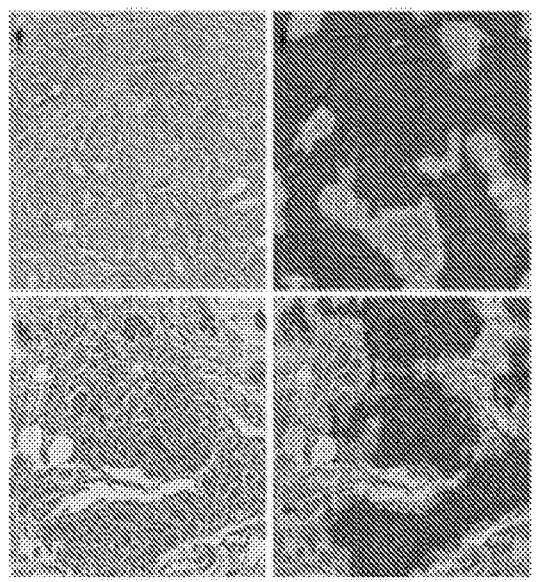
Figure 6C:
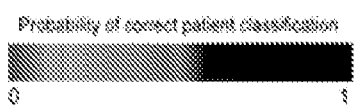

To directly visualize the image components comprising its fingerprint, heat maps of tissue cores, highlighting image regions that most accurately predict patient identity were generated (FIG. 6A). FIG. 6A shows the original H&E images alongside heat maps of patient prediction accuracy using corresponding image regions. Red areas identify the patient accurately, and blue ones do so poorly. Based on the presence of both red and blue areas, some core regions are more predictive of patient identity than others, meaning their patterns are specific to that patient's tumor. FIG. 6B shows an exploded view of two cores. The red-colored regions demonstrate the classifier looks at a combination of stromal and epithelial areas.

Fingerprints Relate to Molecular Status of Breast Cancer

Because each tumor has unique genetic and microenvironmental interactions, it is hypothesized that networks trained to recognize patients would implicitly learn features that reflect the underlying biological processes. For breast cancer, ER/PR/Her2 status is among the most important indicators of prognosis. Hormone-receptor (ER/PR) positive tumors tend to be less aggressive and occur in older patients. Additionally, ER-positive tumors can be treated effectively with drugs that target the estrogen axis. Similarly, Her2-positive tumors can be treated with drugs that target the Her2 axis. For these reasons, the NCCN task force mandate[22] that ER, PR and Her2 status be measured for every new case of breast cancer.

While ER, PR, and Her2 status is routinely assessed by immunohistochemistry (IHC) staining for the receptors (Her2 can also be measured by FISH staining), we explored whether H&E morphology, quantified via fingerprints, could serve as a surrogate marker of these proteins. Initially, we queried this hypothesis on a set of breast cancer images curated TCGA.[12] These samples consist of H&E whole slide images (WSIs) from 939 patients at 40 sites. First, scaled the images to 20× resolution, randomly extracted 120 image patches per image, and fed them through the fingerprint network to calculate fingerprints (FIG. 7A, step 1). Then, a second neural network was trained to compress the fingerprints (512D vectors) into a patch-wise prediction score of a particular receptor from −1 to +1 (FIG. 7A, step 2). For simplicity, the figure indicates the process for predicting ER; however, the same procedure was used for PR and Her2. Finally, the predictions was averaged across the image to estimate the patient's receptor status (FIG. 7A, steps 3-4). We trained on the TCGA dataset with five-fold cross validation. The patients were split into five groups: three were used to train the second network; one was used to monitor training progress and decide when to stop training; the remaining group was tested. The plot in FIG. 7B (left) shows the ROC curve for a representative test set from the TCGA data, for ER classification. The average AUC of the test sets was 0.88 (n=183, per test set). This is the highest ER classification score we have observed, including our previous work using nuclear morphometric features (0.72 AUC)[23] and other recent works that predict molecular characteristics of breast cancer from H&E tissue microarray images.[24-26] To validate these findings, WSIs of 2531 breast cancers were obtained from the ABCTB[13], and tested whether the TCGA-trained classifier could predict ER-status in this group. An AUC of 0.89 on this dataset (n=2531) was measured. Applying the same pipeline to PR and Her2, it was found that fingerprints could predict PR in the TCGA dataset with an average test set AUC=0.78_(n=180, per test set), and AUC=0.81 (ABCTB, n=2514)(FIG. 7B, center and left). The results for Her2 were AUC=0.71 (TCGA, n=124) and AUC=0.79 (ABCTB, n=2487). As a methodological control, in addition to these experiments, we trained a classifier to predict ER status directly from image patches and measured an AUC=0.82 (TCGA, n=138).

The Fingerprint-Based ER Classifier Learned Epithelial Patterns

Figures 8A, 8B:
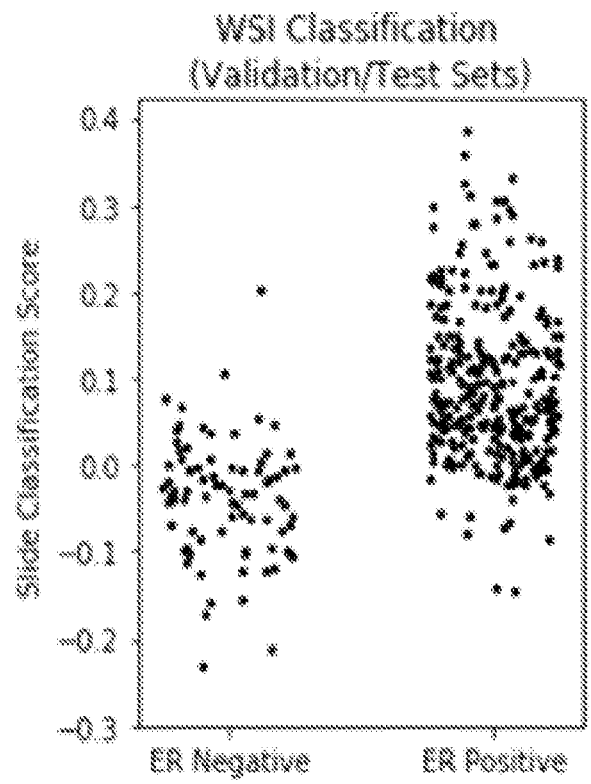

To understand the regions that were used to make biomarker predictions, the trained ER was applied to whole slides. Our first question was whether the ER classifier worked best on epithelium vs. stroma vs. fat. Briefly, each whole slide image was divided into non-overlapping patches and performed image segmentation to classify each patch as epithelium, stroma, fat, or background. Additionally, a 512D tissue fingerprint for each patch was calculated and predictions made ER for each patch. When the patch-predictions were averaged across the entire slide, they were able to classify ER with an AUC of 0.88 (histogram shown in FIG. 8A). The patches were also subset by tissue type and calculated the AUCs after averaging patches of different types (FIG. 8B). It was found that the classifier was most accurate when we pooled predictions from epithelium patches, followed by stroma, followed by fat. Moreover, pooling across epithelium only, or epithelium and stroma was essentially equivalent to pooling across all patches.

Figure 8C:
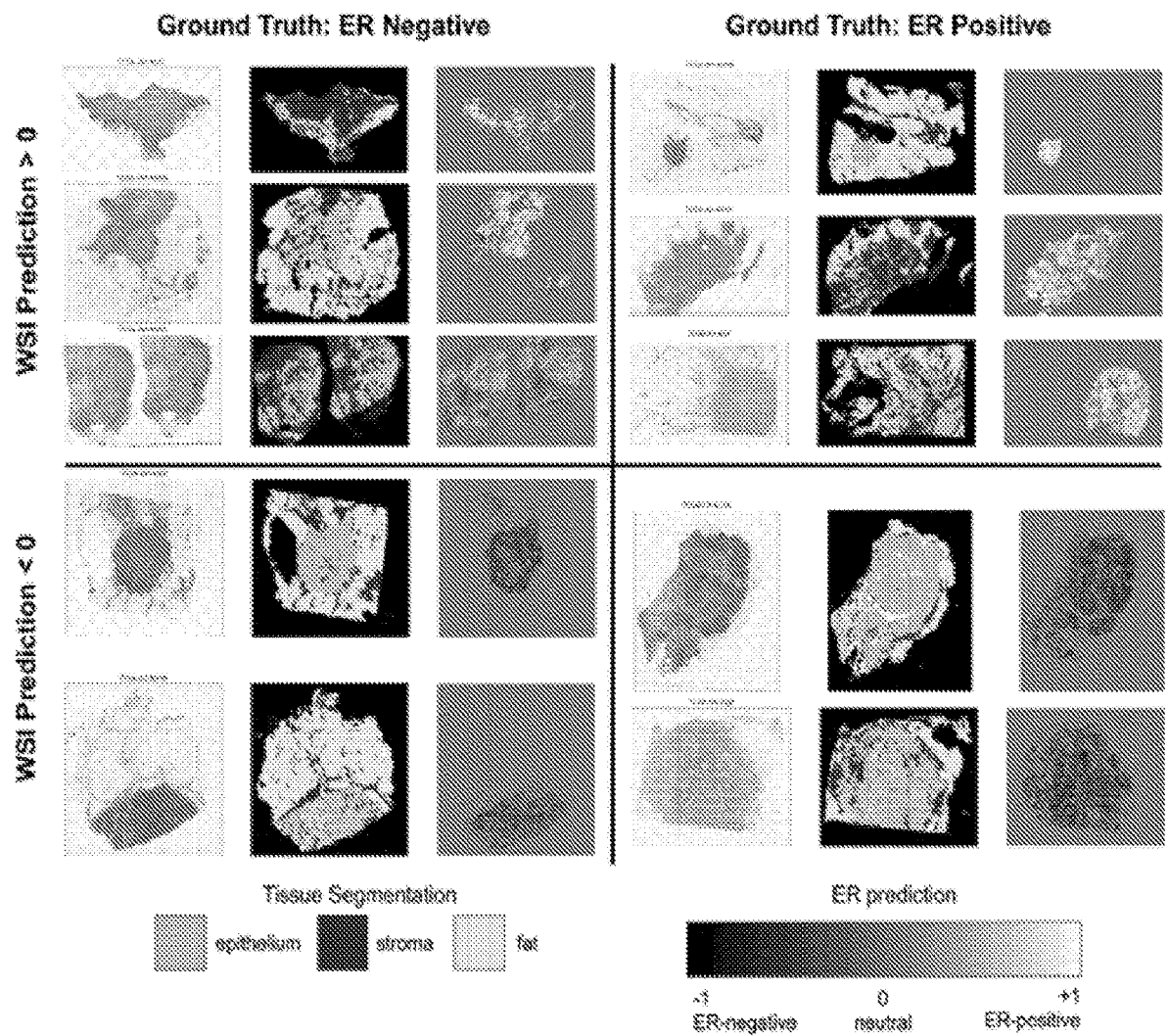

These findings were visually supported by heatmaps generated from the slides (FIG. 8C). We present representative slides that were correctly and incorrectly classified: H&E thumbnails, tissue type segmentations, and ER-prediction heatmaps shaded from black to white representing a prediction of −1 to +1. It was observed that while most areas in the slide have a score of approximately 0 (gray), regions that are strong predictors (white or black) tend to lie in epithelial regions (green). Even when the predictions are inaccurate, the classifier makes mistakes based on misclassifying epithelial regions. For instance, false positive and false negative slides, shown on the upper-left and lower-right quadrants of FIG. 8C show strong white and black signal in epithelial regions.

Figure 9:
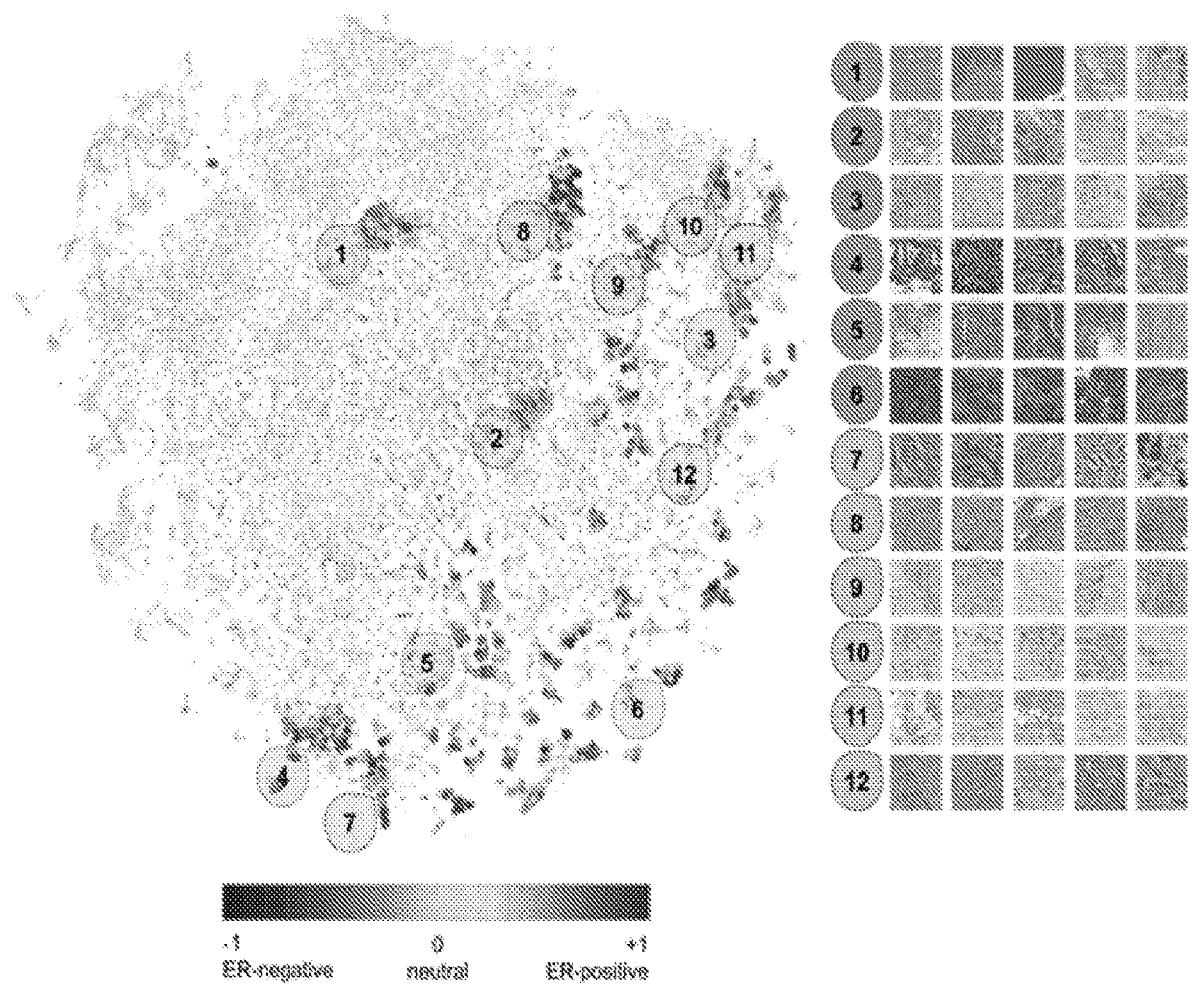
FIG. 9. Left: tSNE embedding of fingerprints from patches extracted from TCGA whole slides, shaded by ER prediction score. 12 clusters with high positive or negative enrichment were selected for manual inspection. Right: H&E patches closest to the cluster centers. Each patch is from a different patient.

A Low Dimensional Embedding of Fingerprints Reveals Histologic Patterns that Predict ER Status To test the hypothesis that tissues predicted to be ER-positive or negative may have similar visual characteristics, fingerprints from whole-slides were embedded into a low dimensional space using a fast implementation of the tSNE algorithm. tSNE is an unsupervised non-linear technique which compresses high dimensional vectors into a low dimensional space, while preserving local structures in the data. In our case, we used tSNE to compress a matrix of fingerprints (512D) into a 2D embedding space (FIG. 9). Each point in this embedding represents a fingerprint from a single patch, and there are 120 patches (points) per WSI on this plot.

When the points by the ER score predicted by the ER-classifier were shaded, it was noticed that most points fail to strongly predict ER status (colored green, prediction approx. 0). However, there were several noticeable clusters of points predicted to be ER-negative (blue) or ER-positive (red). Of these clusters, we manually selected 12 areas to explore (six ER-negative, and six ER-positive), and present the five patches from each cluster. Of note, each patch is from a different patient. Examination of the image patches reveals shared histologic features within each cluster. For instance, cluster 1 reveals regions of necrosis and relatively sparse cells. Patches in cluster 2 include patches with large quantities of immune cells, and cluster 7 contains nests of tumor cells.

Discussion

Deep learning is transforming computer vision and cancer pathology. As training sets scale, there are substantial increases in accuracy on diagnosis, prognosis and theragnosis[27]. However, the biggest gains are likely to come when we learn to leverage a greater spectrum of available pathology images, including the vast majority of images which are mostly or completely unlabeled. Here, we illustrate a novel first step, using tissue matching to discern features that are distinctive for a patient but differ between individuals. While tissue matching is not a skill formally taught in pathology training, it allows a neural network to discover key discriminating histologic features from a large set of unannotated images. Interestingly, these discriminatory features, or fingerprints, tend to reside at the interfaces between epithelial and stromal cells, and may reflect tissue specific genetic and microenvironmental parameters. While this study used serial sections of a TMA to design a rigorous implementation of core-matching, the resulting network trained in experiment 4 demonstrates that a training paradigm that incorporates style normalization may benefit significantly from histology images of any type, not just matched TMA images.

Training a network on the task of tissue identification also improves the interpretability of DNNs and provides insights about the elusive "black box" of deep learning. The ground truth (tissue identify) is indisputable, and visualizations reveal cohesive, biologically interpretable patterns that leverage parameters which are likely to reflect unique underlying genetic and microenvironmental interactions. Hence, we anticipate that fingerprints, which identify features that discriminate between individuals, will be useful when applied to tasks that seek to discriminate between groups of biologically different tissues.

The experiments set forth above demonstrate the significant predictive power of such fingerprints to predict the molecular status of a tumor. Taking the fingerprint network, we extracted fingerprint features from whole slide images and used them to predict ER, PR, and Her2 status from two independent breast cancer cohorts. We initially trained and validated our algorithms on images from The Cancer Genome Atlas (TCGA), with cross-validation. Then, performed independent validation on samples from the Australian Breast Cancer Tissue bank (ABCTB, n=2351) achieving the following areas under the curve: 0.89 (ER), 0.81 (PR), and 0.79 (Her2). These metrics are higher than all previously published attempts to predict molecular information from H&E images. The improved performance is secondary to the implementation of tissue fingerprinting. The performance we found is similar to previous studies assessing the correlation between IHC and microarray assessments of ER and PR, which found good concordance between frozen and IHC for ER (93%) and lower for PR (83%).22,28 We believe that using tissue fingerprints will ultimately enable direct treatment response prediction in breast and other cancers, to an accuracy above that provided by current molecular approaches.

While classification accuracy is an important metric for an algorithm's utility, the significance of fingerprinting extends beyond this, because it enables the interpretation of the histologic patterns learned by deep neural networks. At present, if interpretability is the goal, deep learning is not necessarily the best approach. Using human designed, hand-crafted, pre-extracted features such as cell shape, cell neighborhood statistics can provide rapidly interpretable insights about the tissue properties that correlate to a clinical or molecular outcome.29,30 However, the downside of these approaches is introduction of human bias and the challenge of building workflows to accurately extract these features.

While the flexibility and automaticity of deep learning makes it effective for black box usage in a number of scenarios, interpretability is essential for developing testable hypotheses that advance basic biomedical research. Thus, we were encouraged by the interpretability of our fingerprint-based ER classifier. The prediction heatmaps shown in FIG. 8C demonstrate that the network learned to make positive, negative, and neutral predictions. Thus, it automatically learned to ignore some regions (e.g. neutral, gray areas), while paying attention to others. In this case, it learned to pay attention to areas of tissue epithelium.

A second insight came from plotting the tSNE embedding of fingerprints and discovering natural clusters of patches with similar histologic characteristics predicted to be ER-positive, ER-negative, or neutral (FIG. 9). There is a significant history of histological classification of breast cancer patterns. Numerous attempts have been made to develop histologic typing schemes, but these are subjective, difficult to reproduce, and a large number of slides frequently fall into the "no specified type" category (lacking distinctive characteristics of any pre-defined type). The embedding we present in FIG. 9 provides preliminary support for the development of machine-automated histologic typing, in which tissue patches are clustered by visual/histologic similarity. Of note, our algorithm learned this embedding without knowing the molecular status of the tissues, and the embedding is not sensitive to differences in staining colors. Patches in these clusters have different shades of pink and purple H&E but share core histologic features.

The observation that some of the clusters seem to correlate with ER status suggests a link between tissue architecture and clinical ER status. This view suggests that only a subset of patches/tissue architectures contain useful diagnostic information for making this prediction. Future work will determine whether predicted fingerprints can be used to make biomarker predictions while providing confidence scores based on the quantities and types of tissues present in the slide. Assigning a confidence score to a prediction may facilitate triage and workup of the most relevant biological markers for a particular patient.

An additional area to focus on is how these visualizations can be used to improve a classifier with intermediate accuracy. A potential limitation of this approach is that we demonstrate its application with respect to ER classification, but not PR or HER2. We made this decision believing that focusing on the ER classifier, which had the highest accuracy, would reduce the chances of mis-interpreting the visualizations. However, based on our findings, we believe that using these visualization techniques may provide diagnostic information to troubleshoot difficult classification questions.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

REFERENCES

1. Krizhevsky, A., Sutskever, I. & Hinton, G. E. ImageNet Classification with Deep Convolutional Neural Networks.
2. Ehteshami Bejnordi, B. et al. Diagnostic Assessment of Deep Learning Algorithms for Detection of Lymph Node Metastases in Women With Breast Cancer. JAMA 318, 2199 (2017).
3. Esteva, A. et al. Dermatologist-level classification of skin cancer with deep neural networks. Nature 542, 115-118 (2017).
4. Teare, P., Fishman, M., Benzaquen, O., Toledano, E. & Elnekave, E. Malignancy Detection on Mammography Using Dual Deep Convolutional Neural Networks and Genetically Discovered False Color Input Enhancement. J. Digit. Imaging 30, 499-505 (2017).
5. Liu, Y. et al. Artificial Intelligence-Based Breast Cancer Nodal Metastasis Detection. Arch. Pathol. Lab. Med. (2018). doi:10.5858/arpa.2018-0147-oa
6. Beck, A. H., Irshad, H., Gargeya, R., Khosla, A. & Wang, D. Deep Learning Based Cancer Metastases Detection.
7. Coudray, N. et al. Classification and mutation prediction from non-small cell lung cancer histopathology images using deep learning. Nat. Med. 24, 1559-1567 (2018).
8. Bychkov, D. et al. Deep learning based tissue analysis predicts outcome in colorectal cancer. Sci. Rep. 8, 3395 (2018).
9. Allison, K. H. et al. Understanding diagnostic variability in breast pathology: Lessons learned from an expert consensus review panel. Histopathology 65, 240-251 (2014).
10. Elmore, J. G. et al. Diagnostic Concordance Among Pathologists Interpreting Breast Biopsy Specimens. 98104, 1122-1132 (2017).
11. Robbins, P. et al. Histological grading of breast carcinomas: A study of interobserver agreement. Hum. Pathol. 26, 873-879 (1995).
12. Koboldt, D. C. et al. Comprehensive molecular portraits of human breast tumours. Nature 490, 61-70 (2012).
13. Carpenter, J., Marsh, D., Mariasegaram, M. & Clarke, C. The Australian Breast Cancer Tissue Bank (ABCTB). Open J. Bioresour. 1, e1 (2014).
14. Hammond, M. E. H. et al. American society of clinical oncology/college of American pathologists guideline recommendations for immunohistochemical testing of estrogen and progesterone receptors in breast cancer (unabridged version). Arch. Pathol. Lab. Med. 134, (2010).
15. He, K., Zhang, X., Ren, S. & Sun, J. Deep Residual Learning for Image Recognition.
16. Paszke, A. et al. Automatic differentiation in PyTorch. 31st Conf. Neural Inf. Process. Syst. 1-4 (2017). doi: 10.1017/CBO9781107707221.009
17. Zhu, J.-Y., Park, T., Isola, P. & Efros, A. A. Unpaired Image-to-Image Translation using Cycle-Consistent Adversarial Networks. Proc. IEEE Int. Conf. Comput. Vis. 2017, 2242-2251 (2017).
18. Kather, J. N. et al. Predicting survival from colorectal cancer histology slides using deep learning: A retrospective multicenter study. PLOS Med. 16, e1002730 (2019).
19. Linderman, G. C., Rachh, M., Hoskins, J. G., Steinerberger, S. & Kluger, Y. Fast interpolation-based t-SNE for improved visualization of single-cell RNA-seq data. Nat. Methods 16, 243-245 (2019).
20. Gatys, L. A., Ecker, A. S. & Bethge, M. A Neural Algorithm of Artistic Style. (2015).
21. Van Der Maaten, L. & Hinton, G. Visualizing Data using t-SNE. Journal of Machine Learning Research 9, (2008).
22. Allred, D. et al. NCCN Task Force Report: Estrogen Receptor and Progesterone Receptor Testing in Breast Cancer by Immunohistochemistry. J Natl Compr Canc Netw 7, 1-21 (2009).
23. Rawat, R. R., Ruderman, D., Macklin, P., Rimm, D. L. & Agus, D. B. Correlating nuclear morphometric patterns with estrogen receptor status in breast cancer pathologic specimens. npj Breast Cancer 4, 32 (2018).
24. Couture, H. D. et al. Image analysis with deep learning to predict breast cancer grade, ER status, histologic subtype, and intrinsic subtype. npj Breast Cancer 4, 30 (2018).
25. Shamai, G. et al. Artificial Intelligence Algorithms to Assess Hormonal Status From Tissue Microarrays in Patients With Breast Cancer. 2, 1-14 (2019).
26. Jaber, M. I. et al. A deep learning image-based intrinsic molecular subtype classifier of breast tumors reveals tumor heterogeneity that may affect survival. 1-10 (2020).
27. Campanella, G., Silva, V. W. K. & Fuchs, T. J. Terabyte-scale Deep Multiple Instance Learning for Classification and Localization in Pathology. (2018).
28. Roepman, P. et al. Microarray-Based Determination of Estrogen Receptor, Progesterone Receptor, and HER2 Receptor Status in Breast Cancer. Clin. Cancer Res. 15, 7003-7011 (2009).
29. Yu, K.-H. et al. Predicting non-small cell lung cancer prognosis by fully automated microscopic pathology image features. Nat. Commun. 7, 12474 (2016).
30. Corredor, G. et al. Spatial architecture and arrangement of tumor-infiltrating lymphocytes for predicting likelihood of recurrence in early-stage non-small cell lung cancer. Clin. Cancer Res. clincanres.2013.2018 (2018). doi:10.1158/1078-0432.CCR-18-2013.

What is claimed is:

1. A method for determining a status of a histologic sample of an unknown status, comprising:
    (a) obtaining a trained machine learning model comprising a self-learning neural network, the trained machine learning model obtained by:
        training an untrained machine learning device executing a neural network to form a trained machine learning device by:
        receiving a plurality of digital images of a histologic sample as inputs to a tissue fingerprinting function and outputting a vector of numbers called a tissue fingerprint that describes histologic patterns within the digital image, wherein the untrained machine learning device learns the tissue fingerprinting function by dividing multiple images of characterized or uncharacterized histologic samples into halves, the untrained machine learning device learning said tissue fingerprint that correctly pairs said halves of digital images through an optimization procedure that minimizes an objective loss function including:
            a first component promoting learning of the tissue fingerprinting function that can be used to match digital image patches from the same histologic sample but distinguish said digital image patches from multiple histologic samples; and
            an optional second component of the objective loss function promoting learning of the tissue fingerprinting function that is invariant to sources of pathology artifacts that are encountered during tissue processing;
        wherein the tissue fingerprinting function maps digital images of unannotated stained tissue samples to a tissue fingerprint, wherein the tissue fingerprint comprises a feature vector indicative of histologic patterns within the plurality of digital images; and
    (b) predicting a status of a test stained tissue sample, at least in part by:
        obtaining a sample digital image for a test stained tissue sample; and
        processing the sample digital image using the trained machine learning model to determine a predicted tissue fingerprint for the test stained tissue sample; and
        matching the predicted tissue fingerprint to a set of tissue fingerprints generated from digital images of a set of annotated histologic samples.

2. The method of claim 1, wherein (b) further comprises applying learned correlations between a collection of annotated histologic samples and corresponding tissue fingerprints.

3. The method of claim 1, wherein the tissue fingerprint comprises a diagnostic feature, a prognostic feature, or a theragnostic feature.

4. The method of claim 3, wherein the diagnostic feature, the prognostic feature, or the theragnostic feature comprises a presence or an absence of a biomarker.

5. The method of claim 4, wherein the biomarker is selected from the group consisting of estrogen receptor (ER), human epidermal growth factor receptor 2 (HER2), progesterone receptor (PR), Ki-67, and a cytokeratinmarker.

6. The method of claim 1, wherein the self-learning neural network comprises a convolutional neural network.

7. The method of claim 6, wherein the convolutional neural network comprises a plurality of convolutional layers and a plurality of pooling layers.

8. The method of claim 1, wherein (b) further comprises matching a plurality of tissue fingerprints across a plurality of different tissue regions of the test stained tissue sample.

9. The method of claim 1, wherein the test stained tissue sample is derived from sub-regions of tissue within whole slide images from a tissue block or a core biopsyspecimen.

10. The method of claim 1, wherein the training comprises an optimization procedure that minimizes an objective loss function, wherein the objective loss function promotes learning of the tissue fingerprinting function such that digital image patches from the same sample are matched together and digital image patches from different samples are distinguished from each other.

11. The method of claim 1, wherein the training comprises an optimization procedure that minimizes an objective loss function, wherein the objective loss function promotes learning of the tissue fingerprinting function such that the tissue fingerprinting function is invariant to sources of tissue processing artifacts.

12. The method of claim 11, wherein the objective loss function promotes learning of the tissue fingerprinting function at least in part by: obtaining paired images and penalizing the optimization procedure for learning a tissue fingerprinting function that assigns different fingerprints to the paired images.

13. The method of claim 12, wherein the paired images are obtained at least in part by sectioning a tissue sample that is processed at different laboratories, or at least in part by altering pixels of an original digital image of a tissue sample to simulate an appearance of having been processed at a different laboratory.

14. A method for training a machine learning model comprising a self-learning neural network, comprising:
(a) obtaining a plurality of digital images of a plurality of unannotated stained tissue samples obtained or derived from a plurality of subjects; and
(b) training the self-learning neural network with the plurality of digital images by:
providing the digital images as inputs to a tissue fingerprinting function and outputting a vector of numbers called a tissue fingerprint that describes histologic patterns within each digital image, wherein the tissue fingerprinting function is learned by dividing multiple images of characterized or uncharacterized histologic samples into halves and wherein the tissue fingerprint that correctly pairs said halves of digital images is learned through an optimization procedure that minimizes an objective loss function including:
a first component promoting learning of the tissue fingerprinting function that can be used to match digital image patches from the same histologic sample but distinguish said digital image patches from multiple histologic samples; and,
an optional second component of the objective loss function promoting learning of the tissue fingerprinting function that is invariant to sources of pathology artifacts that are encountered during tissue processing,
wherein the tissue fingerprinting function maps digital images of unannotated stained tissue samples to a tissue fingerprint, wherein the tissue fingerprint comprises a feature vector indicative of histologic patterns within the plurality of digital images.

15. The method of claim 14, wherein the tissue fingerprint comprises a diagnostic feature, a prognostic feature, or a theragnostic feature.

16. The method of claim 15, wherein the diagnostic feature, the prognostic feature, or the theragnostic feature comprises a presence or an absence of a biomarker.

17. The method of claim 16, wherein the biomarker is selected from the group consisting of estrogen receptor (ER), human epidermal growth factor receptor 2 (HER2), progesterone receptor (PR), Ki-67, and a cytokeratin marker.

18. The method of claim 14, wherein the self-learning neural network comprises a convolutional neural network.

19. The method of claim 18, wherein the convolutional neural network comprises a plurality of convolutional layers and a plurality of pooling layers.

20. The method of claim 14, wherein the training comprises an optimization procedure that minimizes an objective loss function, wherein the objective loss function promotes learning of the tissue fingerprinting function such that digital image patches from the same sample are matched together and digital image patches from different samples are distinguished from each other.

21. The method of claim 14, wherein the training comprises an optimization procedure that minimizes an objective loss function, wherein the objective loss function promotes learning of the tissue fingerprinting function such that the tissue fingerprinting function is invariant to sources of tissue processing artifacts.

22. The method of claim 21, wherein the objective loss function promotes learning of the tissue fingerprinting function at least in part by: obtaining paired images and penalizing the optimization procedure for learning a tissue fingerprinting function that assigns different fingerprints to the paired images.

23. The method of claim 22, wherein the paired images are obtained at least in part by sectioning a tissue sample that is processed at different laboratories, or at least in part by altering pixels of an original digital image of a tissue sample to simulate an appearance of having been processed at a different laboratory.

* * * * *